(12) United States Patent
Weers et al.

(10) Patent No.: US 7,442,388 B2
(45) Date of Patent: Oct. 28, 2008

(54) PHOSPHOLIPID-BASED POWDERS FOR DRUG DELIVERY

(76) Inventors: Jeffry G. Weers, 432 Coronado Ave., Half Moon Bay, CA (US) 94019; Thomas E. Tarara, 1233 Paloma Ave., Burlingame, CA (US) 94010; Luis A. Dellamary, 838 Redberry Ct., San Marcos, CA (US) 92069-1846; Jean G. Riess, les Giaines, Falicon (FR) 06950; Ernest G. Schutt, 12139 Ragweed St., San Diego, CA (US) 92129

( * ) Notice: Subject to any disclaimer, the term of this patent is extended or adjusted under 35 U.S.C. 154(b) by 0 days.

(21) Appl. No.: 09/851,226

(22) Filed: May 8, 2001

(65) Prior Publication Data

US 2002/0037316 A1    Mar. 28, 2002

Related U.S. Application Data

(63) Continuation-in-part of application No. 09/568,818, filed on May 10, 2000.

(60) Provisional application No. 60/216,621, filed on Jul. 7, 2000, provisional application No. 60/208,896, filed on Jun. 2, 2000.

(51) Int. Cl.
*A61K 9/14* (2006.01)
*A61K 9/50* (2006.01)

(52) U.S. Cl. .................. 424/489; 424/46; 424/502

(58) Field of Classification Search .............. 424/489, 424/502, 46
See application file for complete search history.

(56) References Cited

U.S. PATENT DOCUMENTS

| | | | |
|---|---|---|---|
| 3,014,844 A | 12/1961 | Thiel et al. | |
| 4,358,442 A * | 11/1982 | Wirtz-Peitz et al. | ......... 424/199 |
| 4,397,799 A | 8/1983 | Edgren et al. | |
| 4,404,228 A | 9/1983 | Cloosterman et al. | |
| 4,571,334 A | 2/1986 | Yoshisa et al. | |
| 4,590,206 A | 5/1986 | Forrester et al. | |
| 4,765,987 A | 8/1988 | Bonte et al. | |
| 4,818,542 A | 4/1989 | DeLuca et al. | |
| 4,904,479 A | 2/1990 | Illum | |
| 5,011,678 A | 4/1991 | Wang et al. | |
| 5,032,585 A | 7/1991 | Lichtenberger | |

(Continued)

FOREIGN PATENT DOCUMENTS

AU          714998        1/1997

(Continued)

OTHER PUBLICATIONS

C. Roth et al., "Production of Hollow Spheres," Pargamon Press, vol. 19 (No. 7), p. 939-942, 1988.

(Continued)

*Primary Examiner*—San-Ming Hui
(74) *Attorney, Agent, or Firm*—Ashok K. Janah; Guy V. Tucker

(57) ABSTRACT

Phospholipid based powders for drug delivery applications are disclosed. The powders comprise a polyvalent cation in an amount effective to increase the gel-to-liquid crystal transition temperature of the particle compared to particles without the polyvalent cation. The powders are hollow and porous and are preferably administered via inhalation.

80 Claims, 3 Drawing Sheets

Effect of Water on pMDI Stability

U.S. PATENT DOCUMENTS

| | | | |
|---|---|---|---|
| 5,069,936 A | 12/1991 | Yen | |
| 5,118,494 A | 6/1992 | Schultz et al. | |
| 5,126,123 A | 6/1992 | Johnson | |
| 5,145,684 A | 9/1992 | Liversidge et al. | |
| 5,173,298 A | 12/1992 | Meadows | |
| 5,182,097 A | 1/1993 | Byron et al. | |
| 5,190,029 A | 3/1993 | Byron et al. | |
| 5,208,226 A | 5/1993 | Palmer | |
| 5,225,183 A | 7/1993 | Purewal | |
| 5,230,884 A | 7/1993 | Evans et al. | |
| 5,254,330 A | 10/1993 | Ganderton et al. | |
| 5,260,306 A | 11/1993 | Boardman et al. | |
| 5,262,405 A | 11/1993 | Girod-Vaquez et al. | |
| 5,284,656 A | 2/1994 | Platz et al. | |
| 5,299,566 A | 4/1994 | Davis et al. | |
| 5,306,483 A | 4/1994 | Mautone | |
| 5,308,620 A | 5/1994 | Yen | |
| 5,348,730 A | 9/1994 | Greenleaf et al. | |
| 5,376,359 A | 12/1994 | Johnson | |
| 5,437,272 A | 8/1995 | Fuhrman | |
| 5,451,569 A | 9/1995 | Wong et al. | |
| 5,470,885 A | 11/1995 | Furhman et al. | |
| 5,474,759 A | 12/1995 | Fassberg et al. | |
| 5,490,498 A | 2/1996 | Faithfull et al. | |
| 5,492,688 A | 2/1996 | Byron et al. | |
| 5,506,203 A | 4/1996 | Backstrom et al. | |
| 5,518,709 A | 5/1996 | Sutton et al. | |
| 5,518,731 A | 5/1996 | Meadows | |
| 5,518,998 A | 5/1996 | Backstrom et al. | |
| 5,527,521 A | 6/1996 | Unger et al. | |
| 5,542,935 A | 8/1996 | Unger et al. | |
| 5,547,656 A | 8/1996 | Unger | |
| 5,562,608 A | 10/1996 | Sekins et al. | |
| 5,569,448 A | 10/1996 | Wong et al. | |
| 5,569,450 A | 10/1996 | Duan et al. | |
| 5,580,575 A | 12/1996 | Unger et al. | |
| 5,605,673 A | 2/1997 | Schutt et al. | |
| 5,605,674 A | 2/1997 | Purewal et al. | |
| 5,612,053 A | 3/1997 | Baichwal | |
| 5,616,311 A | 4/1997 | Yen | |
| 5,635,159 A | 6/1997 | Fu Lu et al. | |
| 5,635,161 A | 6/1997 | Adjei et al. | |
| 5,648,095 A | 7/1997 | Illum et al. | |
| 5,653,961 A | 8/1997 | McNally et al. | |
| 5,653,962 A | 8/1997 | Akehurst et al. | |
| 5,654,007 A | 8/1997 | Johnson et al. | |
| 5,656,297 A | 8/1997 | Bernstein et al. | |
| 5,658,549 A | 8/1997 | Akehurst et al. | |
| 5,667,808 A | 9/1997 | Johnson et al. | |
| 5,667,809 A | 9/1997 | Trevino et al. | |
| 5,674,471 A | 10/1997 | Akehurst et al. | |
| 5,674,472 A | 10/1997 | Akehurst et al. | |
| 5,674,473 A | 10/1997 | Purewal et al. | |
| 5,676,929 A | 10/1997 | Akehurst et al. | |
| 5,681,545 A | 10/1997 | Purewal et al. | |
| 5,683,676 A | 11/1997 | Akehurst et al. | |
| 5,683,677 A | 11/1997 | Purewal et al. | |
| 5,688,782 A | 11/1997 | Neale et al. | |
| 5,690,954 A | 11/1997 | Illum | |
| 5,695,743 A | 12/1997 | Purewal et al. | |
| 5,695,744 A | 12/1997 | Neale et al. | |
| 5,698,537 A | 12/1997 | Pruss | |
| 5,707,352 A | 1/1998 | Sekins et al. | |
| 5,707,644 A | 1/1998 | Illum | |
| 5,718,222 A | 2/1998 | Lloyd et al. | |
| 5,718,921 A | 2/1998 | Mathiowitz et al. | |
| 5,720,940 A | 2/1998 | Purewal et al. | |
| 5,724,957 A | 3/1998 | Rubsamen et al. | |
| 5,725,841 A | 3/1998 | Duan et al. | |
| 5,725,871 A | 3/1998 | Illum | |
| 5,735,263 A | 4/1998 | Rubsamen et al. | |
| 5,736,124 A | 4/1998 | Akehurst et al. | |
| 5,741,478 A | 4/1998 | Osborne et al. | |
| 5,741,522 A | 4/1998 | Violante et al. | |
| 5,743,250 A | 4/1998 | Gonda et al. | |
| 5,743,252 A | 4/1998 | Rubsamen et al. | |
| 5,744,123 A | 4/1998 | Akehurst et al. | |
| 5,744,166 A | 4/1998 | Illum | |
| 5,747,001 A * | 5/1998 | Wiedmann et al. | 424/45 |
| 5,747,445 A | 5/1998 | Backstrom et al. | |
| 5,755,218 A | 5/1998 | Johansson et al. | |
| 5,756,104 A | 5/1998 | de Haan et al. | |
| 5,766,573 A | 6/1998 | Purewal | |
| 5,770,187 A | 6/1998 | Hasebe et al. | |
| 5,770,222 A | 6/1998 | Unger et al. | |
| 5,770,559 A | 6/1998 | Manning et al. | |
| 5,770,585 A | 6/1998 | Kaufman et al. | |
| 5,776,496 A | 7/1998 | Violante et al. | |
| 5,804,212 A | 9/1998 | Illum | |
| 5,811,406 A | 9/1998 | Szoka et al. | |
| 5,814,607 A | 9/1998 | Patton | |
| 5,817,293 A | 10/1998 | Akehurst et al. | |
| 5,820,883 A | 10/1998 | Tice et al. | |
| 5,830,430 A | 11/1998 | Unger et al. | |
| 5,830,853 A | 11/1998 | Backstrom et al. | |
| 5,853,698 A | 12/1998 | Straub et al. | |
| 5,853,752 A | 12/1998 | Unger et al. | |
| 5,853,763 A | 12/1998 | Tice et al. | |
| 5,855,913 A * | 1/1999 | Hanes et al. | 424/489 |
| 5,856,367 A | 1/1999 | Barrows et al. | |
| 5,858,784 A | 1/1999 | Debs et al. | |
| 5,863,554 A | 1/1999 | Illum | |
| 5,874,063 A | 2/1999 | Briggner et al. | |
| 5,874,064 A | 2/1999 | Edwards et al. | |
| 5,891,844 A | 4/1999 | Hafner | |
| 5,898,028 A | 4/1999 | Jensen et al. | |
| 5,925,334 A | 7/1999 | Rubin et al. | |
| 5,955,143 A | 9/1999 | Wheatley | |
| 5,985,309 A | 11/1999 | Edwards et al. | |
| 5,994,318 A * | 11/1999 | Gould-Fogerite et al. | 514/44 |
| 6,017,310 A | 1/2000 | Johnson et al. | |
| 6,051,259 A | 4/2000 | Johnson et al. | |
| 6,068,600 A | 5/2000 | Johnson et al. | |
| 6,113,948 A | 9/2000 | Heath et al. | |
| 6,129,934 A | 10/2000 | Egan et al. | |
| 6,165,508 A | 12/2000 | Tracy et al. | |
| 6,254,854 B1 * | 7/2001 | Edwards et al. | 424/46 |
| 6,309,623 B1 * | 10/2001 | Weers et al. | 424/45 |

FOREIGN PATENT DOCUMENTS

| | | |
|---|---|---|
| CA | 2036844 | 8/1991 |
| CA | 2136704 | 5/1995 |
| EP | 0274431 | 7/1988 |
| EP | 0372777 | 6/1990 |
| EP | 0391896 | 3/1994 |
| EP | 0536204 | 4/1994 |
| EP | 0611567 | 8/1994 |
| EP | 0553298 | 11/1994 |
| EP | 0653205 | 5/1995 |
| EP | 0655237 | 5/1995 |
| EP | 0656205 | 6/1995 |
| EP | 0658101 | 6/1995 |
| EP | 0513127 | 7/1995 |
| EP | 0493437 | 8/1995 |
| EP | 05562556 | 8/1995 |
| EP | 0616525 | 9/1995 |
| EP | 0499344 | 10/1995 |
| EP | 0587790 | 1/1996 |
| EP | 0605578 | 1/1996 |
| EP | 0588897 | 2/1996 |
| EP | 05365235 | 1/1997 |
| EP | 0539522 | 12/1998 |
| GB | 2065659 | * 7/1981 |

| | | | | | | |
|---|---|---|---|---|---|---|
| JP | 03038592 | 2/1991 | | WO | WO9703649 | 2/1997 |
| RU | 91263780 | 12/1991 | | WO | WO9735562 | 10/1997 |
| RU | 92025196 | 6/1992 | | WO | WO9736574 | 10/1997 |
| RU | 93008753 | 5/1993 | | WO | WO9736578 | 10/1997 |
| WO | WO9104011 | 4/1991 | | WO | WO9740819 | 11/1997 |
| WO | WO9111173 | 8/1991 | | WO | WO9741833 | 11/1997 |
| WO | WO9112823 | 9/1991 | | WO | WO9744012 | 11/1997 |
| WO | WO91/16444 | 10/1991 | | WO | WO9744013 | 11/1997 |
| WO | WO9116882 | 11/1991 | | WO | WO9800111 | 1/1998 |
| WO | WO9200107 | 1/1992 | | WO | WO9801161 | 1/1998 |
| WO | WO9214444 | 9/1992 | | WO | WO9805302 | 2/1998 |
| WO | WO9218164 | 10/1992 | | WO | WO9807414 | 2/1998 |
| WO | WO 9218164 | 10/1992 | | WO | WO9808519 | 3/1998 |
| WO | WO9311744 | 6/1993 | | WO | WO9813031 | 4/1998 |
| WO | WO9311745 | 6/1993 | | WO | WO9816205 | 4/1998 |
| WO | WO9314172 | 7/1993 | | WO | WO9817257 | 4/1998 |
| WO | WO9408627 | 4/1994 | | WO | WO9829097 | 7/1998 |
| WO | WO9500128 | 1/1995 | | WO | WO9829098 | 7/1998 |
| WO | WO9505194 | 2/1995 | | WO | WO9829099 | 7/1998 |
| WO | WO9515118 | 6/1995 | | WO | WO9829140 | 7/1998 |
| WO | WO9517195 | 6/1995 | | WO | WO9830207 | 7/1998 |
| WO | WO9523613 | 9/1995 | | WO | WO9831346 | 7/1998 |
| WO | WO9524892 | 9/1995 | | WO | WO9833480 | 8/1998 |
| WO | WO9527476 | 10/1995 | | WO | WO9833487 | 8/1998 |
| WO | WO 9528944 | 11/1995 | | WO | WO9906026 | 2/1999 |
| WO | WO9531182 | 11/1995 | | WO | WO9916419 | 4/1999 |
| WO | WO9531964 | 11/1995 | | WO | WO9726863 | 7/1999 |
| WO | WO 9637399 | 3/1996 | | WO | WO9932083 | 7/1999 |
| WO | WO9609814 | 4/1996 | | WO | WO 0113892 | 3/2001 |
| WO | WO96109814 | 4/1996 | | | | |
| WO | WO9615814 | 5/1996 | | | | |
| WO | WO9618388 | 6/1996 | | | | |
| WO | WO9619197 | 6/1996 | | | | |
| WO | WO9619198 | 6/1996 | | | | |
| WO | WO9619199 | 6/1996 | | | | |
| WO | WO9619968 | 7/1996 | | | | |
| WO | WO9626746 | 9/1996 | | | | |
| WO | WO9632149 | 10/1996 | | | | |
| WO | WO9640068 | 12/1996 | | | | |
| WO | WO 9640277 | 12/1996 | | | | |

OTHER PUBLICATIONS

Abdellaziz Ben-Jebria et al., "Large Porous Particles for Sustained Protection from Carbachol-Induced Brnchoconstriction in Guinea Pigs," Pharm Res, vol. 16 (No. 4), p. 555-561.

Zarif et al., "Amphotericin B Cochleates as a Novel Oral Delivery System," International Symposium, p. 964-965.

Hauser et al., "Interactions of Divalent Cations with Phosphatidylserine Bilayer Membranes," Biochem., p. 34-41.

* cited by examiner

SEM photomicrographs depicting the effect the of calcium on the morphology of spray-dried DSPC particles; (A) Ca/DSPC = 1; (B) Ca/DSPC = 0.5; (C) Ca/DSPC = 0.25; (D) Ca/DSPC = 0

PHOSPHOLIPID-BASED POWDERS FOR DRUG DELIVERY

RELATED APPLICATIONS

This application claims the priority of U.S. Provisional Application 60/208,896 filed Jun. 2, 2000 and U.S. Provisional Application 60/216,621 filed Jul. 7, 2000 and is a continuation-in-part of U.S. Ser. No. 09/568,818, filed May 10, 2000.

FIELD OF THE INVENTION

The present invention relates to particulate compositions suitable for drug delivery, preferably via inhalation. In particular, the present invention provides phospholipid-containing particulate compositions comprising a polyvalent cation. The particulate compositions of the present invention exhibit an increased gel-to-liquid crystal transition temperatures resulting in improved dispersibility and storage stability.

BACKGROUND OF THE INVENTION

Phospholipids are major components of cell and organelle membranes, blood lipoproteins, and lung surfactant. In terms of pulmonary drug delivery, phospholipids have been investigated as therapeutic agents for the treatment of respiratory distress syndrome (i.e. exogenous lung surfactants), and as suitable excipients for the delivery of actives. The interaction of phospholipids with water is critical to the formation, maintenance, and function of each of these important biological complexes (McIntosh and Magid). At low temperatures in the gel phase, the acyl chains are in a conformationally well-ordered state, essentially in the all-trans configuration. At higher temperatures, above the chain melting temperature, this chain order is lost, owing to an increase in gauche conformer content (Seddon and Cevc).

Several exogenous lung surfactants have been marketed and include products derived from bovine lungs (Survanta®, Abbott Laboratories), porcine lungs (CuroSurf®, Dey Laboratories), or completely synthetic surfactants with no apoproteins (e.g. ALEC®, ExoSurf® Glaxo Wellcome). To date, these products have been utilized for the treatment of infant respiratory distress syndrome (IRDS). None have been successful in receiving FDA approval for the treatment of adult respiratory distress syndrome (ARDS). The current infant dose is 100 mg/kg. For a 50 kg adult, this would translate into a dose of 5 g. A dose of this amount can only be administered to ARDS patients by direct instillation into the patient's endotracheal tube, or possibly via nebulization of aqueous dispersions of the surfactant material.

Instillation of surfactants leads to deposition primarily in the central airways, and little of the drug makes it to the alveoli, where it is needed to improve gas exchange in these critically ill patients. Nebulization of surfactant may allow for greater peripheral delivery, but is plagued by the fact that (a) current nebulizers are inefficient devices and only ca. 10% of the drug actually reaches the patients lungs; (b) the surfactant solutions foam during the nebulization process, leading to complications and further loss of drug. It is believed that as much as 99% of the administered surfactant may be wasted due to poor delivery to the patient. If more effective delivery of surfactant could be achieved, it is likely that the administered dose and cost for treatment of ARDS could be dramatically decreased.

Further, lung surfactant has been shown to modulate mucous transport in airways. In this regard, the chronic administration of surfactant for the treatment of patients with chronic obstructive pulmonary disease (COPD) has been suggested. Still other indications with significantly lower doses may be open to treatment if a dry powder form of a lung surfactant were available. The powdered surfactant formulation may be purely synthetic (i.e. with no added apoproteins). Alternatively, the powder formulation could contain the hydrophobic apoproteins SP-B or SP-C or alternative recombinant or synthetic peptide mimetics (e.g. $KL_4$).

Due to its spreading characteristics on lung epithelia, surfactant has been proposed as the ideal carrier for delivery of drugs to the lung, and via the lung to the systemic circulation. Once again, achieving efficient delivery to the lung is important, especially in light of the potential high cost of many of the current products. One potential way to deliver drugs in phospholipids is as a dry powder aerosolized to the lung. Most fine powders (<5 μm) exhibit poor dispersibility. This can be problematic when attempting to deliver, aerosolize, and/or package the powders.

The major forces that control particle-particle interactions can be divided into short and long range forces. Long-range forces include gravitational attractive forces and electrostatics, where the interaction varies as the square of the separation distance. Short-range attractive forces dominate for dry powders and include van der Waals interactions, hydrogen bonding, and liquid bridging. Liquid bridging occurs when water molecules are able to irreversibly bind particles together.

Phospholipids are especially difficult to formulate as dry powders as their low gel to liquid crystal transition temperature (Tm) values and amorphous nature lead to powders which are very sticky and difficult to deaggregate and aerosolize. Phospholipids with Tm values less than 10° C. (e.g. egg PC or any unsaturated lipids) form highly cohesive powders following spray-drying. Inspection of the powders via scanning electron microscopy reveals highly agglomerated particles with surfaces that appear to have been melted/annealed. Formulating phospholipid powders which have low Tm are problematic, especially if one hopes to achieve a certain particle morphology, as in the case of aerosol delivery. Thus, it would be advantageous to find ways to elevate the Tm of these lipids. Examples of particulate compositions incorporating a surfactant are disclosed in PCT publications WO 99/16419, WO 99/38493, WO 99/66903, WO 00/10541, and U.S. Pat. Nos. 5,855,913, which are hereby incorporated in their entirety by reference.

Currently, lung surfactant is given to patients by intubating them and instilling a suspension of lung surfactant directly into the lungs. This is a highly invasive procedure which generally is not performed on conscious patients, and as do most procedures, carries its own risks. Potential applications for lung surfactant beyond the current indication of respiratory distress syndrome in neonates are greatly limited by this method of administration. For example, lung surfactant may be useful in a variety of disease states that are, in part, due to decreased lung surfactant being present in the lungs. U.S. Pat. Nos. 5,451,569, 5,698,537, and 5,925,337, and PCT publications WO 97/26863 and WO 00/27360, for example, disclose the pulmonary administration of lung surfactant to treat various conditions, the disclosures of which are hereby incorporated in their entirety by reference. Diseases that are thought to be possibly aggravated by lung surfactant deficiency include cystic fibrosis, chronic obstructive pulmonary disease, and asthma, just to name a few. The delivery of exogenous lung surfactant, in a topical fashion, to patients suffering from these diseases may ameliorate certain signs and symptoms of the diseases. For chronic conditions, the regular (once or more times per day on a prolonged basis) delivery of lung surfactant via intubation and instillation to ambulatory patients is impractical. Further, because of their high surface activity, lung surfactant suspensions are not amenable to nebulization due to foaming. The current delivery of phospholipid-based preparations by instillation or nebulization are highly inefficient in delivering material to the peripheral lung. Therefore, the ability to deliver lung surfactant to patients via dry powder inhalation would be a tremendous advantage over the current method, since it would avoid the need for intubation, thereby expanding the potential uses of lung surfactant in the clinical setting.

SUMMARY OF THE INVENTION

The present invention provides for dry powder compositions of phospholipid suitable for drug delivery. According to a preferred embodiment, the phospholipid compositions are efficiently delivered to the deep lung. The phospholipid may be delivered alone, as in the case of lung surfactant or in combination with another active agent and/or excipient. The use of dry powder compositions may also open new indications for use since the patient need not be intubated. According to one embodiment, the compositions of the present invention may be delivered from a simple passive DPI device. The present compositions allow for greater stability on storage, and for more efficient delivery to the lung.

It has been found in the present work that the gel to liquid crystal phase transition of the phospholipid, Tm, is critical in obtaining phospholipid-based dry powders that both flow well, and are readily dispersible from a dry powder inhaler device. The present invention is related to the use of polyvalent cations, preferably divalent cations to dramatically increase the Tm of phospholipids. As used herein, "polyvalent cations" refers to polyvalent salts or their ionic components. Increasing the Tm of the phospholipid leads to the following formulation improvements: (a) Increases in Tm allows the formulator to increase the inlet and outlet temperatures on the spray-drier, or on a vacuum oven during a secondary drying step. Higher temperatures allow the drying phase of the spray-drying to be controllable over a wider temperature range, thereby facilitating removal of trapped blowing agent used in the manufacture of powders according to one aspect of the present invention; (b) Increases in Tm allow for a large difference between Tm and the storage temperature, thereby improving powder stability; (c) Increases in Tm yield phospholipids in the gel state, where they are less prone to taking up water and water bridging phenomena (d) Increases in Tm yield phospholipids which are able to spread more effectively upon contact with lung epithelia than hydrated phospholipids, thereby allowing drugs to be more effectively distributed to the lung periphery; (e) Increases in Tm dramatically improves the dispersibility of the resulting powders, thereby improving the emitted dose and fine particle fraction following pulmonary delivery.

According to a preferred embodiment, the present invention relates to highly dispersible dry powder compositions of phospholipids suitable for pulmonary delivery. The compositions according to the present invention are useful as synthetic lung surfactants for the treatment of local lung conditions (e.g. asthma, COPD), or as carriers for the pulmonary delivery of active agents, including small molecules, peptides, proteins, DNA, and immunologic agents.

One aspect of the present invention is to provide powdered, dispersible compositions having stable dispersibility over time. The compositions exhibit a characteristic gel to liquid crystal phase transition temperature, Tm, which is greater than a recommended storage temperature, Ts, typically room temperature, by at least 20° C. Preferably Tm is at least 40° C. greater than Ts.

It is a further aspect of the present invention that the increases in Tm afforded by addition of divalent cations leads to the ability to dry the powders in a secondary drying step at temperatures (Td) up to the Tm of the lipid. As well, it is possible to increase the inlet and outlet temperatures on a spray-drier should a spray-dry process be employed (Td≈Tm).

It is a further aspect of the present invention to provide a powdered, dispersible form of a lung surfactant having stable dispersibility over time and excellent spreading characteristics on an aqueous subphase.

It is a further aspect of the present invention that the improvements in dispersibility obtained by the present compositions allow for a simple, passive inhaler device to be utilized, in spite of the fact that particles less than 5 μm are contemplated and generally preferred. Present state-of-the-art formulations for fine particles utilize blends with large lactose particles to improve dispersibility. When placed in a passive DPI device such formulations exhibit a strong dependence of emitted dose and lung deposition on the patient's inspiratory flowrate. The present compositions exhibit little flowrate dependence on the emitted dose and lung deposition.

BRIEF DESCRIPTION OF THE DRAWINGS

FIG. 2 are SEM photographs the effect of calcium ion concentration on the morphology of spray-dried particles according to the invention.

DEFINITIONS

Figure 1:
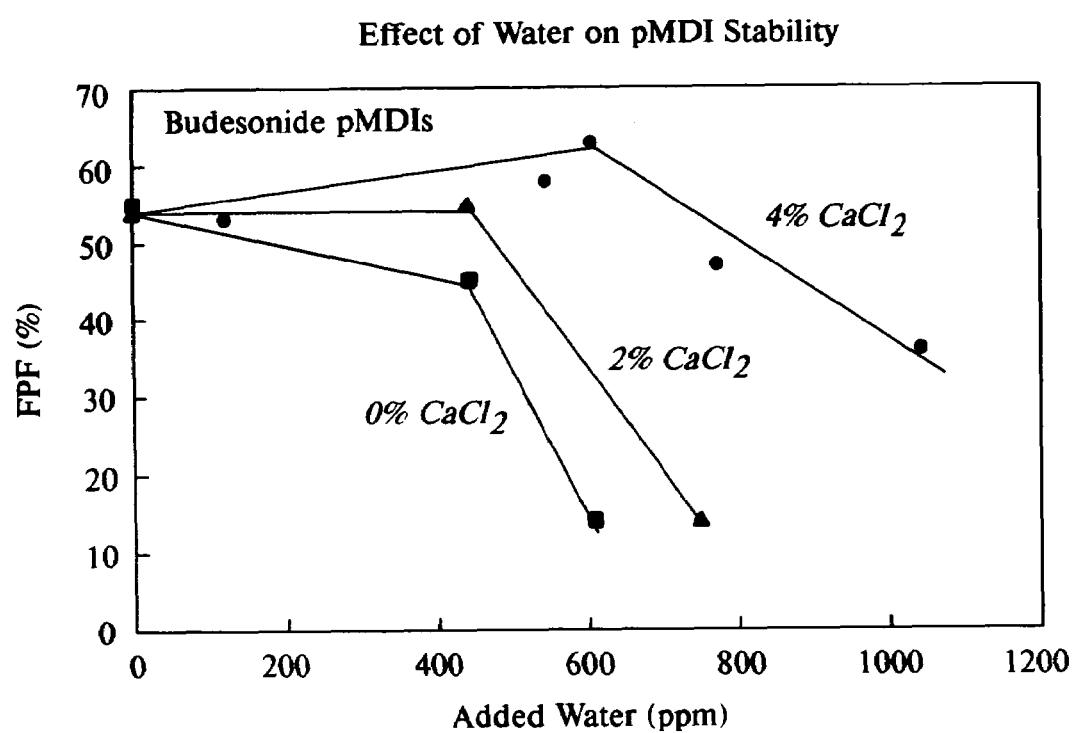
FIG. 1 is a graph depicting the physical stability of budesonide in pMDI.
Figure 3:
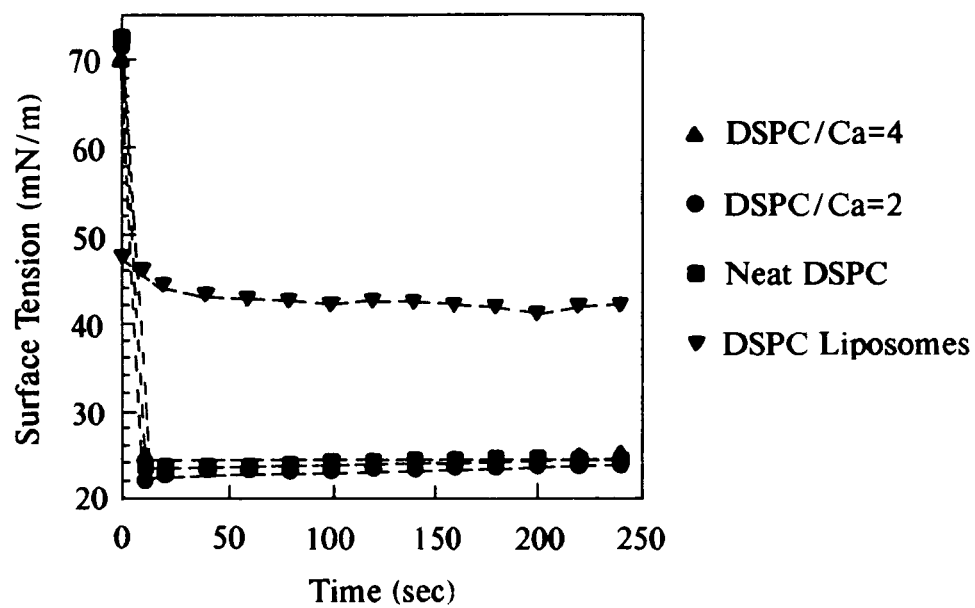
FIG. 3 is a graph depicting the spreading characteristics of powders of the instant invention.

"Active agent" as described herein includes an agent, drug, compound, composition of matter or mixture thereof which provides some diagnostic, prophylactic, or pharmacologic, often beneficial, effect. This includes foods, food supplements, nutrients, drugs, vaccines, vitamins, and other beneficial agents. As used herein, the terms further include any physiologically or pharmacologically active substance that produces a localized or systemic effect in a patient. The active agent that can be delivered includes antibiotics, antibodies, antiviral agents, anepileptics, analgesics, anti-inflammatory agents and bronchodilators, and viruses and may be inorganic and organic compounds, including, without limitation, drugs which act on the peripheral nerves, adrenergic receptors, cholinergic receptors, the skeletal muscles, the cardiovascular system, smooth muscles, the blood circulatory system, synaptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, polysaccharides, steroids, hypnotics and sedatives, psychic energizers, tranquilizers, anticonvulsants, muscle relaxants, antiparkinson agents, analgesics, anti-inflammatories, muscle contractants, antimicrobials, antimalarials, hormonal agents including contraceptives, sympathomimetics, polypeptides, and proteins capable of eliciting physiological effects, diuretics, lipid regulating agents, antiandrogenic agents, antiparasitics, neoplastics, antineoplastics, hypoglycemics, nutritional agents and supplements, growth supplements, fats, antienteritis agents, electrolytes, vaccines and diagnostic agents.

Examples of active agents useful in this invention include but are not limited to insulin, calcitonin, erythropoietin (EPO), Factor VIII, Factor IX, ceredase, cerezyme, cyclosporine, granulocyte colony stimulating factor (GCSF), alpha-1 proteinase inhibitor, elcatonin, granulocyte macrophage colony stimulating factor (GMCSF), growth hormone, human growth hormone (hGH), growth hormone releasing hormone (GHRH), heparin, low molecular weight heparin (LMWH), interferon alpha, interferon beta, interferon gamma, interleukin-2, luteinizing hormone releasing hormone (LHRH), leuprolide, somatostatin, somatostatin analogs including octreotide, vasopressin analog, follicle stimulating hormone (FSH), immunoglobulins, insulin-like growth factor, insulintropin, interleukin-1 receptor antagonist, interleukin-3, interleukin-4, interleukin-6, macrophage colony stimulating factor (M-CSF), nerve growth factor, parathyroid hormone (PTH), thymosin alpha 1, IIb/IIIa inhibitor, alpha-1 antitrypsin, respiratory syncytial virus antibody, cystic fibrosis transmembrane regulator (CFTR) gene, deoxyribonuclease (Dnase), bactericidal/permeability increasing protein (BPI), anti-CMV antibody, interleukin-1 receptor, 13-cis retinoic acid, nicotine, nicotine bitartrate, gentamicin, ciprofloxacin, amphotericin, amikacin, tobramycin, pentamidine isethionate, albuterol sulfate, metaproterenol sulfate, beclomethasone dipropionate, triamcinolone acetamide, budesonide acetonide, ipratropium bromide, flunisolide, fluticasone, fluticasone propionate, salmeterol xinofoate, formeterol fumarate, cromolyn sodium, ergotamine tartrate and the analogues, agonists and antagonists of the above. Active agents may further comprise nucleic acids, present as bare nucleic acid molecules, viral vectors, associated viral particles, nucleic acids associated or incorporated within lipids or a lipid-containing material, plasmid DNA or RNA or other nucleic acid construction of a type suitable for transfection or transformation of cells, particularly cells of the alveolar regions of the lungs. The active agents may be in various forms, such as soluble and insoluble charged or uncharged molecules, components of molecular complexes or pharmacologically acceptable salts. The active agents may be naturally occurring molecules or they may be recombinantly produced, or they may be analogs of the naturally occurring or recombinantly produced active agents with one or more amino acids added or deleted. Further, the active agent may comprise live attenuated or killed viruses suitable for use as vaccines.

As used herein, the term "emitted dose" or "ED" refers to an indication of the delivery of dry powder from a suitable inhaler device after a firing or dispersion event from a powder unit or reservoir. ED is defined as the ratio of the dose delivered by an inhaler device (described in detail below) to the nominal dose (i.e., the mass of powder per unit dose placed into a suitable inhaler device prior to firing). The ED is an experimentally-determined amount, and is typically determined using an in-vitro device set up which mimics patient dosing. To determine an ED value, a nominal dose of dry powder (as defined above) is placed into a suitable dry powder inhaler, which is then actuated, dispersing the powder. The resulting aerosol cloud is then drawn by vacuum from the device, where it is captured on a tared filter attached to the device mouthpiece. The amount of powder that reaches the filter constitutes the delivered dose. For example, for a 5 mg, dry powder-containing blister pack placed into an inhalation device, if dispersion of the powder results in the recovery of 4 mg of powder on a tared filter as described above, then the ED for the dry powder composition is: 4 mg (delivered dose)/5 mg (nominal dose)×100=80%.

"Mass median diameter" or "MMD" is a measure of mean particle size, since the powders of the invention are generally polydisperse (i.e., consist of a range of particle sizes). MMD values as reported herein are determined by laser diffraction, although any number of commonly employed techniques can be used for measuring mean particle size.

"Mass median aerodynamic diameter" or "MMAD" is a measure of the aerodynamic size of a dispersed particle. The aerodynamic diameter is used to describe an aerosolized powder in terms of its settling behavior, and is the diameter of a unit density sphere having the same settling velocity, generally in air, as the particle. The aerodynamic diameter encompasses particle shape, density and physical size of a particle. As used herein, MMAD refers to the midpoint or median of the aerodynamic particle size distribution of an aerosolized powder determined by cascade impaction.

DETAILED DESCRIPTION OF THE INVENTION

The present invention is directed to the formulation of dry phospholipid-polyvalent cation based particulate composition. In particular, the present invention is directed to the use of polyvalent cations in the manufacture of phospholipid-containing, dispersible particulate compositions for pulmonary administration to the respiratory tract for local or systemic therapy via aerosolization, and to the particulate compositions made thereby. The invention is based, at least in part, on the surprising discovery of the beneficial aerosolization and stabilization properties of phospholipid-containing particulate compositions comprising a polyvalent cation. These unexpected benefits include a dramatic increase in the gel-to-liquid crystal phase transition temperature (Tm) of the particulate composition, improved dispersibility of such particulate compositions, improved spreadability of the particulate compositions upon contact with lung epithelia thereby allowing drugs to be more effectively distributed to the lung periphery, and improved storage stability of the particulate compositions.

It is surprisingly unexpected that the addition of a very hygroscopic salt such as calcium chloride would stabilize a dry powder prone to moisture induced destabilization, as one would expect that the calcium chloride would readily pick up water leading to particle aggregation. However, this is not what is observed. In contrast, addition of calcium ions leads to a dramatic improvement in the stability of the dry phospholipid-based powder to humidity. While not being bound to any theory, it is believed that calcium ions are believed to intercalate the phospholipid membrane, thereby interacting directly with the negatively charged portion of the zwitterionic headgroup. The result of this interaction is increased dehydration of the headgroup area and condensation of the acyl-chain packing, all of which leads to increased thermodynamic stability of the phospholipids.

The polyvalent cation for use in the present invention is preferably a divalent cation including calcium, magnesium, zinc, iron, and the like. According to the invention, the polyvalent cation is present in an amount effective to increase the Tm of the phospholipid such that the particulate composition exhibits a Tm which is greater than its storage temperature Ts by at least 20° C., preferably at least 40° C. The molar ratio of polyvalent cation to phospholipid should be at least 0.05, preferably 0.05-2.0, and most preferably 0.25-1.0. A molar ratio of polyvalent cation:phospholipid of about 0.50 is particularly preferred according to the present invention. Calcium is the particularly preferred polyvalent cation of the present invention and is provided as calcium chloride.

In a broad sense, phospholipid suitable for use in the present invention include any of those known in the art.

According to a preferred embodiment, the phospholipid is most preferably a saturated phospholipid. According to a particularly preferred embodiment, saturated phosphatidylcholines are used as the phospholipid of the present invention. Preferred acyl chain lengths are 16:0 and 18:0 (i.e. palmitoyl and stearoyl). According to one embodiment directed to lung surfactant compositions, the phospholipid can make up to 90 to 99.9% w/w of the composition. Suitable phospholipids according to this aspect of the invention include natural or synthetic lung surfactants such as those commercially available under the trademarks ExoSurf, InfaSurf® (Ony, Inc.), Survanta, CuroSurf, and ALEC. For drug delivery purposes wherein an active agent is included with the particulate composition, the phospholipid content will be determined by the drug activity, the mode of delivery, and other factors and will likely be in the range from about 20% to up to 99.9% w/w. Thus, drug loading can vary between about 0.1% and 80% w/w, preferably 5-70% w/w.

According to a preferred embodiment, it has been found in the present work that the Tm of the phospholipid is critical in obtaining phospholipid-based dry powders that both flow well and are readily dispersible from a dry powder inhaler (DPI). The Tm of the modified lipid microparticles can be manipulated by varying the amount of polyvalent cations in the formulation.

Phospholipids from both natural and synthetic sources are compatible with the present invention and may be used in varying concentrations to form the structural matrix. Generally compatible phospholipids comprise those that have a gel to liquid crystal phase transition greater than about 40° C. Preferably the incorporated phospholipids are relatively long chain (i.e. $C_{16}$-$C_{22}$) saturated lipids and more preferably comprise saturated phospholipids, most preferably saturated phosphatidylcholines having acyl chain lengths of 16:0 or 18:0 (palmitoyl and stearoyl). Exemplary phospholipids useful in the disclosed stabilized preparations comprise, phosphoglycerides such as dipalmitoylphosphatidylcholine, disteroylphosphatidylcholine, diarachidoylphosphatidylcholine dibehenoylphosphatidylcholine, diphosphatidyl glycerol, short-chain phosphatidylcholines, long-chain saturated phosphatidylethanolamines, long-chain saturated phosphatidylserines, long-chain saturated phosphatidylglycerols, long-chain saturated phosphatidylinositols.

In addition to the phospholipid, a co-surfactant or combinations of surfactants, including the use of one or more in the liquid phase and one or more associated with the particulate compositions are contemplated as being within the scope of the invention. By "associated with or comprise" it is meant that the particulate compositions may incorporate, adsorb, absorb, be coated with or be formed by the surfactant. Surfactants include fluorinated and nonfluorinated compounds and are selected from the group consisting of saturated and unsaturated lipids, nonionic detergents, nonionic block copolymers, ionic surfactants and combinations thereof. In those embodiments comprising stabilized dispersions, such nonfluorinated surfactants will preferably be relatively insoluble in the suspension medium. It should be emphasized that, in addition to the aforementioned surfactants, suitable fluorinated surfactants are compatible with the teachings herein and may be used to provide the desired preparations.

Compatible nonionic detergents suitable as co-surfactants comprise: sorbitan esters including sorbitan trioleate (Span™ 85), sorbitan sesquioleate, sorbitan monooleate, sorbitan monolaurate, polyoxyethylene (20) sorbitan monolaurate, and polyoxyethylene (20) sorbitan monooleate, oleyl polyoxyethylene (2) ether, stearyl polyoxyethylene (2) ether, lauryl polyoxyethylene (4) ether, glycerol esters, and sucrose esters. Other suitable nonionic detergents can be easily identified using McCutcheon's Emulsifiers and Detergents (McPublishing Co., Glen Rock, N.J.) which is incorporated herein in its entirety. Preferred block copolymers include diblock and triblock copolymers of polyoxyethylene and polyoxypropylene, including poloxamer 188 (Pluronic™ F-68), poloxamer 407 (Pluronic™ F-127), and poloxamer 338. Ionic surfactants such as sodium sulfosuccinate, and fatty acid soaps may also be utilized.

Other lipids including glycolipids, ganglioside GM1, sphingomyelin, phosphatidic acid, cardiolipin; lipids bearing polymer chains such as polyethylene glycol, chitin, hyaluronic acid, or polyvinylpyrrolidone; lipids bearing sulfonated mono-, di-, and polysaccharides; fatty acids such as palmitic acid, stearic acid, and oleic acid; cholesterol, cholesterol esters, and cholesterol hemisuccinate may also be used in accordance with the teachings of this invention.

It will further be appreciated that the particulate compositions according to the invention may, if desired, contain a combination of two or more active ingredients. The agents may be provided in combination in a single species of particulate composition or individually in separate species of particulate compositions. For example, two or more active agents may be incorporated in a single feed stock preparation and spray dried to provide a single particulate composition species comprising a plurality of active agents. Conversely, the individual actives could be added to separate stocks and spray dried separately to provide a plurality of particulate composition species with different compositions. These individual species could be added to the suspension medium or dry powder dispensing compartment in any desired proportion and placed in the aerosol delivery system as described below. Further, as alluded to above, the particulate compositions (with or without an associated agent) may be combined with one or more conventional (e.g. a micronized drug) active or bioactive agents to provide the desired dispersion stability or powder dispersibility.

Based on the foregoing, it will be appreciated by those skilled in the art that a wide variety of active agents may be incorporated in the disclosed particulate compositions. Accordingly, the list of preferred active agents above is exemplary only and not intended to be limiting. It will also be appreciated by those skilled in the art that the proper amount of agent and the timing of the dosages may be determined for the particulate compositions in accordance with already existing information and without undue experimentation.

In addition to the phospholipid and polyvalent cation, the microparticles of the present invention may also include a biocompatible, preferably biodegradable polymer, copolymer, or blend or other combination thereof. In this respect useful polymers comprise polylactides, polylactide-glycolides, cyclodextrins, polyacrylates, methylcellulose, carboxymethylcellulose, polyvinyl alcohols, polyanhydrides, polylactams, polyvinyl pyrrolidones, polysaccharides (dextrans, starches, chitin, chitosan, etc.), hyaluronic acid, proteins, (albumin, collagen, gelatin, etc.). Examples of polymeric resins that would be useful for the preparation of perforated ink microparticles include: styrene-butadiene, styrene-isoprene, styrene-acrylonitrile, ethylene-vinyl acetate, ethylene-acrylate, ethylene-acrylic acid, ethylene-methylacrylatate, ethylene-ethyl acrylate, vinyl-methyl methacrylate, acrylic acid-methyl methacrylate, and vinyl chloride-vinyl acetate. Those skilled in the art will appreciate that, by selecting the appropriate polymers, the delivery efficiency of the particulate compositions and/or the stability of the dispersions may be tailored to optimize the effectiveness of the active or agent.

Besides the aforementioned polymer materials and surfactants, it may be desirable to add other excipients to a particulate composition to improve particle rigidity, production yield, emitted dose and deposition, shelf-life and patient acceptance. Such optional excipients include, but are not limited to: coloring agents, taste masking agents, buffers, hygroscopic agents, antioxidants, and chemical stabilizers. Further, various excipients may be incorporated in, or added to, the particulate matrix to provide structure and form to the particulate compositions (i.e. microspheres such as latex particles). In this regard it will be appreciated that the rigidifying components can be removed using a post-production technique such as selective solvent extraction.

Other excipients may include, but are not limited to, carbohydrates including monosaccharides, disaccharides and polysaccharides. For example, monosaccharides such as dextrose (anhydrous and monohydrate), galactose, mannitol, D-mannose, sorbitol, sorbose and the like; disaccharides such as lactose, maltose, sucrose, trehalose, and the like; trisaccharides such as raffinose and the like; and other carbohydrates such as starches (hydroxyethylstarch), cyclodextrins and maltodextrins. Other excipients suitable for use with the present invention, including amino acids, are known in the art such as those disclosed in WO 95/31479, WO 96/32096, and WO 96/32149. Mixtures of carbohydrates and amino acids are further held to be within the scope of the present invention. The inclusion of both inorganic (e.g. sodium chloride, etc.), organic acids and their salts (e.g. carboxylic acids and their salts such as sodium citrate, sodium ascorbate, magnesium gluconate, sodium gluconate, tromethamine hydrochloride, etc.) and buffers is also contemplated. The inclusion of salts and organic solids such as ammonium carbonate, ammonium acetate, ammonium chloride or camphor are also contemplated.

Yet other preferred embodiments include particulate compositions that may comprise, or may be coated with, charged species that prolong residence time at the point of contact or enhance penetration through mucosae. For example, anionic charges are known to favor mucoadhesion while cationic charges may be used to associate the formed microparticulate with negatively charged bioactive agents such as genetic material. The charges may be imparted through the association or incorporation of polyanionic or polycationic materials such as polyacrylic acids, polylysine, polylactic acid and chitosan.

According to a preferred embodiment, the particulate compositions may be used in the form of dry powders or in the form of stabilized dispersions comprising a non-aqueous phase. Accordingly, the dispersions or powders of the present invention may be used in conjunction with metered dose inhalers (MDIs), dry powder inhalers (DPIs), atomizers, nebulizers or liquid dose instillation (LDI) techniques to provide for effective drug delivery. With respect to inhalation therapies, those skilled in the art will appreciate that the hollow and porous microparticles of the present invention are particularly useful in DPIs. Conventional DPIs comprise powdered formulations and devices where a predetermined dose of medicament, either alone or in a blend with lactose carrier particles, is delivered as an aerosol of dry powder for inhalation.

The medicament is formulated in a way such that it readily disperses into discrete particles with an MMD between 0.5 to 20 μm, preferably 0.5-5 μm, and are further characterized by an aerosol particle size distribution less than about 10 μm mass median aerodynamic diameter (MMAD), and preferably less than 5.0 μm. The mass median aerodynamic diameters of the powders will characteristically range from about 0.5-10 μm, preferably from about 0.5-5.0 μm MMAD, more preferably from about 1.0-4.0 μm MMAD.

The powder is actuated either by inspiration or by some external delivery force, such as pressurized air. Examples of DPIs suitable for administration of the particulate compositions of the present invention are disclosed in U.S. Pat. Nos. 5,740,794, 5,785,049, 5,673,686, and 4,995,385 and PCT application Nos. 00/72904, 00/21594, and 01/00263, hereby incorporated in their entirety by reference. DPI formulations are typically packaged in single dose units such as those disclosed in the above mentioned patents or they employ reservoir systems capable of metering multiple doses with manual transfer of the dose to the device.

As discussed above, the stabilized dispersions disclosed herein may also be administered to the nasal or pulmonary air passages of a patient via aerosolization, such as with a metered dose inhaler. The use of such stabilized preparations provides for superior dose reproducibility and improved lung deposition as disclosed in WO 99/16422, hereby incorporated in its entirety by reference. MDIs are well known in the art and could easily be employed for administration of the claimed dispersions without undue experimentation. Breath activated MDIs, as well as those comprising other types of improvements which have been, or will be, developed are also compatible with the stabilized dispersions and present invention and, as such, are contemplated as being within the scope thereof. However, it should be emphasized that, in preferred embodiments, the stabilized dispersions may be administered with an MDI using a number of different routes including, but not limited to, topical, nasal, pulmonary or oral. Those skilled in the art will appreciate that, such routes are well known and that the dosing and administration procedures may be easily derived for the stabilized dispersions of the present invention.

Along with the aforementioned embodiments, the stabilized dispersions of the present invention may also be used in conjunction with nebulizers as disclosed in PCT WO 99/16420, the disclosure of which is hereby incorporated in its entirety by reference, in order to provide an aerosolized medicament that may be administered to the pulmonary air passages of a patient in need thereof. Nebulizers are well known in the art and could easily be employed for administration of the claimed dispersions without undue experimentation. Breath activated nebulizers, as well as those comprising other types of improvements which have been, or will be, developed are also compatible with the stabilized dispersions and present invention and are contemplated as being with in the scope thereof.

Along with DPIs, MDIs and nebulizers, it will be appreciated that the stabilized dispersions of the present invention may be used in conjunction with liquid dose instillation or LDI techniques as disclosed in, for example, WO 99/16421 hereby incorporated in its entirety by reference. Liquid dose instillation involves the direct administration of a stabilized dispersion to the lung. In this regard, direct pulmonary administration of bioactive compounds is particularly effective in the treatment of disorders especially where poor vascular circulation of diseased portions of a lung reduces the effectiveness of intravenous drug delivery. With respect to LDI the stabilized dispersions are preferably used in conjunction with partial liquid ventilation or total liquid ventilation. Moreover, the present invention may further comprise introducing a therapeutically beneficial amount of a physiologically acceptable gas (such as nitric oxide or oxygen) into the pharmaceutical microdispersion prior to, during or following administration.

Particularly preferred embodiments of the invention incorporate spray dried, hollow and porous particulate compositions as disclosed in WO 99/16419, hereby incorporated in its entirety by reference. Such particulate compositions comprise particles having a relatively thin porous wall defining a large internal void, although, other void containing or perforated structures are contemplated as well. In preferred embodiments the particulate compositions will further comprise an active agent.

Compositions according to the present invention typically yield powders with bulk densities less than 0.5 g/cm$^3$ or 0.3 g/cm$^3$, preferably less 0.1 g/cm$^3$ and most preferably less than 0.05 g/cm$^3$. By providing particles with very low bulk density, the minimum powder mass that can be filled into a unit dose container is reduced, which eliminates the need for carrier particles. That is, the relatively low density of the powders of the present invention provides for the reproducible administration of relatively low dose pharmaceutical compounds. Moreover, the elimination of carrier particles will potentially minimize throat deposition and any "gag" effect, since the large lactose particles will impact the throat and upper airways due to their size.

It will be appreciated that the particulate compositions disclosed herein comprise a structural matrix that exhibits, defines or comprises voids, pores, defects, hollows, spaces, interstitial spaces, apertures, perforations or holes. The absolute shape (as opposed to the morphology) of the perforated microstructure is generally not critical and any overall configuration that provides the desired characteristics is contemplated as being within the scope of the invention. Accordingly, preferred embodiments can comprise approximately microspherical shapes. However, collapsed, deformed or fractured particulates are also compatible.

In accordance with the teachings herein the particulate compositions will preferably be provided in a "dry" state. That is the microparticles will possess a moisture content that allows the powder to remain chemically and physically stable during storage at ambient temperature and easily dispersible. As such, the moisture content of the microparticles is typically less than 6% by weight, and preferably less 3% by weight. In some instances the moisture content will be as low as 1% by weight. Of course it will be appreciated that the moisture content is, at least in part, dictated by the formulation and is controlled by the process conditions employed, e.g., inlet temperature, feed concentration, pump rate, and blowing agent type, concentration and post drying.

Reduction in bound water leads to significant improvements in the dispersibility and flowability of phospholipid based powders, leading to the potential for highly efficient delivery of powdered lung surfactants or particulate composition comprising active agent dispersed in the phospholipid. The improved dispersibility allows simple passive DPI devices to be used to effectively deliver these powders.

Although the powder compositions are preferably used for inhalation therapies, the powders of the present invention can also be administered by other techniques known in the art, including, but not limited to intramuscular, intravenous, intratracheal, intraperitoneal, subcutaneous, and transdermal, either as dry powders, reconstituted powders, or suspensions.

As seen from the passages above, various components may be associated with, or incorporated in the particulate compositions of the present invention. Similarly, several techniques may be used to provide particulates having the desired morphology (e.g. a perforated or hollow/porous configuration), dispersibility and density. Among other methods, particulate compositions compatible with the instant invention may be formed by techniques including spray drying, vacuum drying, solvent extraction, emulsification or lyophilization, and combinations thereof. It will further be appreciated that the basic concepts of many of these techniques are well known in the prior art and would not, in view of the teachings herein, require undue experimentation to adapt them so as to provide the desired particulate compositions.

While several procedures are generally compatible with the present invention, particularly preferred embodiments typically comprise particulate compositions formed by spray drying. As is well known, spray drying is a one-step process that converts a liquid feed to a dried particulate form. With respect to pharmaceutical applications, it will be appreciated that spray drying has been used to provide powdered material for various administrative routes including inhalation. See, for example, M. Sacchetti and M. M. Van Oort in: Inhalation Aerosols: Physical and Biological Basis for Therapy, A. J. Hickey, ed. Marcel Dekkar, New York, 1996, which is incorporated herein by reference.

In general, spray drying consists of bringing together a highly dispersed liquid, and a sufficient volume of hot air to produce evaporation and drying of the liquid droplets. The preparation to be spray dried or feed (or feed stock) can be any solution, course suspension, slurry, colloidal dispersion, or paste that may be atomized using the selected spray drying apparatus. In preferred embodiments the feed stock will comprise a colloidal system such as an emulsion, reverse emulsion, microemulsion, multiple emulsion, particulate dispersion, or slurry. Typically the feed is sprayed into a current of warm filtered air that evaporates the solvent and conveys the dried product to a collector. The spent air is then exhausted with the solvent. Those skilled in the art will appreciate that several different types of apparatus may be used to provide the desired product. For example, commercial spray dryers manufactured by Buchi Ltd. or Niro Corp. will effectively produce particles of desired size.

It will further be appreciated that these spray dryers, and specifically their atomizers, may be modified or customized for specialized applications, i.e. the simultaneous spraying of two solutions using a double nozzle technique. More specifically, a water-in-oil emulsion can be atomized from one nozzle and a solution containing an anti-adherent such as mannitol can be co-atomized from a second nozzle. In other cases it may be desirable to push the feed solution though a custom designed nozzle using a high pressure liquid chromatography (HPLC) pump. Provided that microstructures comprising the correct morphology and/or composition are produced the choice of apparatus is not critical and would be apparent to the skilled artisan in view of the teachings herein. Examples of spray drying methods and systems suitable for making the dry powders of the present invention are disclosed in U.S. Pat. Nos. 6,077,543, 6,051,256, 6,001,336, 5,985,248, and 5,976,574, hereby incorporated in their entirety by reference.

While the resulting spray-dried powdered particles typically are approximately spherical in shape, nearly uniform in size and frequently are hollow, there may be some degree of irregularity in shape depending upon the incorporated medicament and the spray drying conditions. In many instances dispersion stability and dispersibility of the particulate compositions appears to be improved if an inflating agent (or blowing agent) is used in their production as disclosed in WO 99/16419 cited above. Particularly preferred embodiments comprise an emulsion with the inflating agent as the disperse or continuous phase. The inflating agent is preferably dispersed with a surfactant solution, using, for instance, a commercially available microfluidizer at a pressure of about 5000 to 15,000 psi. This process forms an emulsion, preferably stabilized by an incorporated surfactant, typically comprising submicron droplets of water immiscible blowing agent dispersed in an aqueous continuous phase. The formation of such emulsions using this and other techniques are common and well known to those in the art. The blowing agent is preferably a fluorinated compound (e.g. perfluorohexane, perfluorooctyl bromide, perfluorooctyl ethane, perfluorodecalin, perfluorobutyl ethane) which vaporizes during the spray-drying process, leaving behind generally hollow, porous aerodynamically light microspheres. Other suitable liquid blowing agents include nonfluorinated oils, chloroform, Freons, ethyl acetate, alcohols and hydrocarbons. Nitrogen and carbon dioxide gases are also contemplated as a suitable blowing agent. Perfluorooctyl ethane is particularly preferred according to the invention.

Besides the aforementioned compounds, inorganic and organic substances which can be removed under reduced pressure by sublimation in a post-production step are also compatible with the instant invention. These sublimating compounds can be dissolved or dispersed as micronized crystals in the spray drying feed solution and include ammonium carbonate and camphor. Other compounds compatible with the present invention comprise rigidifying solid structures which can be dispersed in the feed solution or prepared in-situ. These structures are then extracted after the initial particle generation using a post-production solvent extraction step. For example, latex particles can be dispersed and subsequently dried with other wall forming compounds, followed by extraction with a suitable solvent.

Although the particulate compositions are preferably formed using a blowing agent as described above, it will be appreciated that, in some instances, no additional blowing agent is required and an aqueous dispersion of the medicament and/or excipients and surfactant(s) are spray dried directly. In such cases, the formulation may be amenable to process conditions (e.g., elevated temperatures) that may lead to the formation of hollow, relatively porous microparticles. Moreover, the medicament may possess special physicochemical properties (e.g., high crystallinity, elevated melting temperature, surface activity, etc.) that makes it particularly suitable for use in such techniques.

Regardless of which blowing agent is ultimately selected, it has been found that compatible particulate compositions may be produced particularly efficiently using a Büchi mini spray drier (model B-191, Switzerland). As will be appreciated by those skilled in the art, the inlet temperature and the outlet temperature of the spray drier are not critical but will be of such a level to provide the desired particle size and to result in a product that has the desired activity of the medicament. In this regard, the inlet and outlet temperatures are adjusted depending on the melting characteristics of the formulation components and the composition of the feed stock. The inlet temperature may thus be between 60° C. and 170° C., with the outlet temperatures of about 40° C. to 120° C. depending on the composition of the feed and the desired particulate characteristics. Preferably these temperatures will be from 90° C. to 120° C. for the inlet and from 60° C. to 90° C. for the outlet. The flow rate which is used in the spray drying equipment will generally be about 3 ml per minute to about 15 ml per minute. The atomizer air flow rate will vary between values of 25 liters per minute to about 50 liters per minute. Commercially available spray dryers are well known to those in the art, and suitable settings for any particular dispersion can be readily determined through standard empirical testing, with due reference to the examples that follow. Of course, the conditions may be adjusted so as to preserve biological activity in larger molecules such as proteins or peptides.

Whatever components are selected, the first step in particulate production typically comprises feed stock preparation. If the phospholipid based particle is intended to act as a carrier for another active agent, the selected active agent is dissolved in a solvent, preferably water, to produce a concentrated solution. The polyvalent cation may be added to the active agent solution or may be added to the phospholipid emulsion as discussed below. The active agent may also be dispersed directly in the emulsion, particularly in the case of water insoluble agents. Alternatively, the active agent may be incorporated in the form of a solid particulate dispersion. The concentration of the active agent used is dependent on the amount of agent required in the final powder and the performance of the delivery device employed (e.g., the fine particle dose for a MDI or DPI). As needed, cosurfactants such as poloxamer 188 or span 80 may be dispersed into this annex solution. Additionally, excipients such as sugars and starches can also be added.

In selected embodiments a polyvalent cation-containing oil-in-water emulsion is then formed in a separate vessel. The oil employed is preferably a fluorocarbon (e.g., perfluorooctyl bromide, perfluorooctyl ethane, perfluorodecalin) which is emulsified with a phospholipid. For example, polyvalent cation and phospholipid may be homogenized in hot distilled water (e.g., 60° C.) using a suitable high shear mechanical mixer (e.g., Ultra-Turrax model T-25 mixer) at 8000 rpm for 2 to 5 minutes. Typically 5 to 25 g of fluorocarbon is added dropwise to the dispersed surfactant solution while mixing. The resulting polyvalent cation-containing perfluorocarbon in water emulsion is then processed using a high pressure homogenizer to reduce the particle size. Typically the emulsion is processed at 12,000 to 18,000 psi, 5 discrete passes and kept at 50 to 80° C.

The active agent solution and perfluorocarbon emulsion are then combined and fed into the spray dryer. Typically the two preparations will be miscible as the emulsion will preferably comprise an aqueous continuous phase. While the bioactive agent is solubilized separately for the purposes of the instant discussion it will be appreciated that, in other embodiments, the active agent may be solubilized (or dispersed) directly in the emulsion. In such cases, the active emulsion is simply spray dried without combining a separate active agent preparation.

In any event, operating conditions such as inlet and outlet temperature, feed rate, atomization pressure, flow rate of the drying air, and nozzle configuration can be adjusted in accordance with the manufacturer's guidelines in order to produce the required particle size, and production yield of the resulting dry particles. Exemplary settings are as follows: an air inlet temperature between 60° C. and 170° C.; an air outlet between 40° C. to 120° C.; a feed rate between 3 ml to about 15 ml per minute; and an aspiration air flow of 300 L/min. and an atomization air flow rate between 25 to 50 L/min. The selection of appropriate apparatus and processing conditions are well within the purview of a skilled artisan in view of the teachings herein and may be accomplished without undue experimentation. In any event, the use of these and substantially equivalent methods provide for the formation of hollow porous aerodynamically light microparticles with particle diameters appropriate for aerosol deposition into the lung. microstructures that are both hollow and porous, almost honeycombed or foam-like in appearance. In especially preferred embodiments the particulate compositions comprise hollow, porous spray dried microparticles.

Along with spray drying, particulate compositions useful in the present invention may be formed by lyophilization. Those skilled in the art will appreciate that lyophilization is a freeze-drying process in which water is sublimed from the composition after it is frozen. The particular advantage associated with the lyophilization process is that biologicals and pharmaceuticals that are relatively unstable in an aqueous solution can be dried without elevated temperatures (thereby eliminating the adverse thermal effects), and then stored in a dry state where there are few stability problems. With respect to the instant invention such techniques are particularly compatible with the incorporation of peptides, proteins, genetic material and other natural and synthetic macromolecules in particulate compositions without compromising physiological activity. Methods for providing lyophilized particulates are known to those of skill in the art and it would clearly not require undue experimentation to provide dispersion compatible microparticles in accordance with the teachings herein. The lyophilized cake containing a fine foam-like structure can be micronized using techniques known in the art to provide 3 to 10 µm sized particles. Accordingly, to the extent that lyophilization processes may be used to provide microparticles having the desired porosity and size they are in conformance with the teachings herein and are expressly contemplated as being within the scope of the instant invention.

Besides the aforementioned techniques, the particulate compositions or particles of the present invention may also be formed using a method where a feed solution (either emulsion or aqueous) containing wall forming agents is rapidly added to a reservoir of heated oil (e.g. perflubron or other high boiling FCs) under reduced pressure. The water and volatile solvents of the feed solution rapidly boils and are evaporated. This process provides a perforated structure from the wall forming agents similar to puffed rice or popcorn. Preferably the wall forming agents are insoluble in the heated oil. The resulting particles can then separated from the heated oil using a filtering technique and subsequently dried under vacuum.

Additionally, the particulate compositions of the present invention may also be formed using a double emulsion method. In the double emulsion method the medicament is first dispersed in a polymer dissolved in an organic solvent (e.g. methylene chloride, ethyl acetate) by sonication or homogenization. This primary emulsion is then stabilized by forming a multiple emulsion in a continuous aqueous phase containing an emulsifier such as polyvinylalcohol. Evaporation or extraction using conventional techniques and apparatus then removes the organic solvent. The resulting microspheres are washed, filtered and dried prior to combining them with an appropriate suspension medium in accordance with the present invention Whatever production method is ultimately selected for production of the particulate compositions, the resulting powders have a number of advantageous properties that make them particularly compatible for use in devices for inhalation therapies. In particular, the physical characteristics of the particulate compositions make them extremely effective for use in dry powder inhalers and in the formation of stabilized dispersions that may be used in conjunction with metered dose inhalers, nebulizers and liquid dose instillation. As such, the particulate compositions provide for the effective pulmonary administration of active agents.

In order to maximize dispersibility, dispersion stability and optimize distribution upon administration, the mean geometric particle size of the particulate compositions is preferably about 0.5-50 µm, more preferably 1-20 µm and most preferably 0.5-5 µm. It will be appreciated that large particles (i.e. greater than 50 µm) may not be preferred in applications where a valve or small orifice is employed, since large particles tend to aggregate or separate from a suspension which could potentially clog the device. In especially preferred embodiments the mean geometric particle size (or diameter) of the particulate compositions is less than 20 µm or less than 10 µm. More preferably the mean geometric diameter is less than about 7 µm or 5 µm, and even more preferably less than about 2.5 µm. Other preferred embodiments will comprise preparations wherein the mean geometric diameter of the particulate compositions is between about 1 µm and 5 µm. In especially preferred embodiments the particulate compositions will comprise a powder of dry, hollow, porous microspherical shells of approximately 1 to 10 µm or 1 to 5 µm in diameter, with shell thicknesses of approximately 0.1 µm to approximately 0.5 µm. It is a particular advantage of the present invention that the particulate concentration of the dispersions and structural matrix components can be adjusted to optimize the delivery characteristics of the selected particle size.

Although preferred embodiments of the present invention comprise powders and stabilized dispersions for use in pharmaceutical applications, it will be appreciated that the particulate compositions and disclosed dispersions may be used for a number of non pharmaceutical applications. That is, the present invention provides particulate compositions which have a broad range of applications where a powder is suspended and/or aerosolized. In particular, the present invention is especially effective where an active or bioactive ingredient must be dissolved, suspended or solubilized as fast as possible. By increasing the surface area of the porous microparticles or by incorporation with suitable excipients as described herein, will result in an improvement in dispersibility, and/or suspension stability. In this regard, rapid dispersement applications include, but are not limited to: detergents, dishwasher detergents, food sweeteners, condiments, spices, mineral flotation detergents, thickening agents, foliar fertilizers, phytohormones, insect pheromones, insect repellents, pet repellents, pesticides, fungicides, disinfectants, perfumes, deodorants, etc.

The foregoing description will be more fully understood with reference to the following Examples. Such Examples, are, however, merely representative of preferred methods of practicing the present invention and should not be read as limiting the scope of the invention.

EXAMPLE I

Effect of Added Calcium Ions on the Tm of Spray-Dried Phospholipids

The effect of calcium ions on the gel-to-liquid crystal transition temperature (Tm) of spray-dried phospholipids was investigated. The resulting powders were examined visually for powder flow characteristics, characterized for Tm using a differential scanning calorimeter (DSC).

Dry lung surfactant particles comprising long-chain saturated phosphatidylcholines, PCs (e.g., dipalmitoylphosphatidylcholine, DPPC or distearoylphosphatidylcholine, DSPC) and varying amounts of calcium chloride were manufactured by an emulsion-based spray-drying process. Calcium levels were adjusted as mole ratio equivalents relative to the PC present, with Ca/PC (mol/mol)=0 to 1. Accordingly, 1 g of saturated phosphatidylcholine (Genzyme Corp, Cambridge, Mass.) and 0 to 0.18 g of calcium chloride dihydrate (Fisher Scientific Corp., Pittsburgh, Pa.) were dispersed in approximately 40 mL of hot deionized water (T=60-70° C.) using an Ultra-Turrax T-25 mixer at 8,000-10,000 rpm for 2 to 5 minutes. 18 g of perfluorooctyl ethane, PFOE (F-Tech, Tokyo, Japan) was then added dropwise during mixing at a rate of 2-5 ml/min. After the addition was complete, the emulsion was mixed for an additional period of not less than 4 minutes at 10,000-12,000 rpm. The resulting coarse emulsion was then homogenized under high pressure with an Avestin C-5 homogenizer (Ottawa, Canada) at 8,000-10,000 psi for 4 passes, and at 18,000-20,000 psi for a final pass.

The submicron fluorocarbon-in-water emulsion was then spray-dried with a Buchi B-191 Mini Spray-Drier (Flawil, Switzerland), equipped with a modified 2-fluid atomizer under the following conditions: inlet temperature=85° C.; outlet temperature=58°-61° C.; pump=1.9 ml min$^{-1}$; atomizer pressure=60-65 psig; atomizer flow rate=30-35 cm. The aspiration flow (69-75%) was adjusted to maintain an exhaust bag pressure=20-21 mbar.

The spray-dried phospholipid particles were collected using the standard Buchi cyclone separator. The volume-weighted mean geometric diameter (VMD) of the dry phospholipid particles was confirmed by laser diffraction (Sympatech Helos H1006, Clausthal-Zellerfeld, Germany), and ranged from 2.5 μm to 3.8 μm depending on the formulation.

The resulting dry phospholipid particles were also characterized using a model 2920 DSC (TA Instruments) and by a Karl Fisher moisture analyzer. Approximately 0.5 to 2 mg dry powder was weighed into aluminum sample pans and hermetically sealed. Each sample was analyzed using a modulated DSC mode under the following conditions: equilibration at −20° C., and 2° C./min ramp to 150° C. modulated +/−1° C. every 60 sec. The phospholipid Tm was defined as the peak maxima of the first endothermic transition from each reversing heat flow thermogram. For moisture analysis, approximately 50 mg powder was suspended in 1 mL of anhydrous dimethylforamide (DMF). The suspension was then injected directly into the titration cell and the moisture content was derived. The residual moisture content in the spray-dried DSPC particles is shown in Table Ia, and was found to decrease as a function of Ca/PC mole ratio. Tables Ib and Ic present the Tm values for the various spray-dried PC particles as a function of the Ca/PC ratio. Hydrated DSPC and DPPC liposomes exhibit Tm values of 58 and 42° C., respectively. Dramatic increases in Tm were observed following spray-drying, and with increases in calcium content. The powder formulations devoid of calcium ions were highly cohesive, while the formulations incorporating added calcium were free-flowing powders.

The present example illustrates that the hydration status of powdered phospholipid preparations greatly influences their inherent thermodynamic and physicochemical characteristics, i.e., Tm and flow properties. Increases in phospholipid Tm are believed to directly correlate with increases in thermal stability, which could lead to an enhancement in long-term storage stability. In addition, decreased moisture content may also lead to greater chemical stability.

TABLE Ia

Effect of Added Calcium on the Residual Moisture Content of Spray-Dried DSPC

| Ca/DSPC (mol/mol) | Water Content (%) |
|---|---|
| 0 | 2.9 |
| 0.25 | 1.9 |
| 0.50 | 1.4 |

TABLE Ib

Effect of Added Calcium on the Tm of Spray-dried DSPC

| Ca/DSPC (mol/mol) | Tm (° C.) |
|---|---|
| 0 (hydrated) | 58 |
| 0 | 79 |
| 0.25 | 85 |
| 0.5 | 98 |
| 1.0 | 126 |

TABLE Ic

Effect of Added Calcium on the Tm of Spray-dried DPPC

| Ca/DPPC (mol/mol) | Tm (° C.) |
|---|---|
| 0 (hydrated) | 42 |
| 0 | 63 |
| 0.25 | 69 |
| 0.5 | 89 |

EXAMPLE II

Effect of Added Magnesium Ions on Tm of Spray-Dried Phospholipids

Phospholipid particles stabilized with magnesium ions were prepared by an emulsion-based spray-drying technique. The emulsion feedstock was prepared according to the procedure described below. In the first step, 0.45 g of distearoylphosphatidylcholine, DSPC, and 0.126 g magnesium chloride hexahydrate (Fisher Scientific, Pittsburgh, Pa.) were dispersed in 41 g of hot deionized water (T=60 to 70° C.) using an Ultra-Turrax mixer (model T-25) at 10,000 rpm for 2 min. 17 g of perfluorooctyl ethane was then added drop wise at a rate of approximately 1-2 ml/min during mixing. After the fluorocarbon addition was complete, the emulsion was mixed for an additional period of not less than 4 minutes. The resulting coarse emulsion was then processed through a high pressure homogenizer (Avestin, Ottawa, Canada) at 18,000 psi for 5 passes, to yield a submicron fluorocarbon-in-water emulsion stabilized by a monolayer of DSPC. The emulsion was then spray-dried with a Buchi model B-191 Mini Spray-Drier under the following spray conditions: aspiration=69%, inlet temperature=85° C., outlet temperature=58° C., feed pump=1.9 mL min$^{-1}$, and atomizer flow rate=33 cm.

Differential scanning calorimetric analysis of the dry particles revealed the Tm for the DSPC in the powder was 88° C. as compared with 79° C. for neat DSPC (Table Ib). This foregoing example illustrates the effect ions such as magnesium have upon the thermodynamic properties of dry phospholipid particles.

EXAMPLE III

Preparation of Spray-Dried Lung Surfactant (ExoSurf®) Particles

Dry lung surfactant particles having the same components as ExoSurf® (Glaxo-Wellcome, Research Triangle Park, N.C.) were manufactured using a spray-drying process. To achieve this end, the osmotic NaCl component of Exosurf was replaced in one formulation by CaCl$_2$. Accordingly, 1.55 g of dipalmitoylphosphatidylcholine and 0.144 g of calcium chloride dihydrate or sodium chloride were dispersed in 50 mL of hot deionized water (T=60-70° C.) using an Ultra-Turrax T-25 mixer at 8,000-10,000 rpm for 2 min. 18.5 g of perfluorooctyl ethane was then added dropwise during mixing at a rate of 2-5 ml/min. After the addition was complete, the emulsion was mixed for an additional period of not less than 4 minutes at 10,000-12,000 rpm. The resulting coarse emulsion was then homogenized under high pressure with an Avestin C-5 homogenizer (Ottawa, Canada) at 8,000-10,000 psi for 4 passes, and at 18,000-20,000 psi for a final pass. In a separate flask, 0.12 g of Tyloxapol® was dispersed in 10 g of hot deionized water (T=60-70° C.). The Tyloxapol dispersion was then decanted into a vial that contained 0.174 g of cetyl alcohol. The vial was sealed and the cetyl alcohol was dispersed by placing it in a sonication bath for 15 minutes. The Tyloxapol/cetyl alcohol dispersion was added to the fluorocarbon emulsion and mixed for 5 min. The feed solution was then spray-dried with a Bucchi-191 Mini Spray-Drier, equipped with a modified 2-fluid atomizer under the following conditions: inlet temperature=85° C., outlet temperature=58°-61° C., pump=1.9 ml min$^{-1}$, atomizer pressure=60-65 psig, atomizer flow rate=30-35 cm. The aspiration flow (69-75%) was adjusted to maintain an exhaust bag pressure=20-21 mbar. A free flowing white powder was collected using the standard Buchi cyclone separator.

The spray-dried powders were manually filled into a proprietary blister package and heat-sealed. The filling procedure was performed in a humidity controlled glove box (RH<2%). All blister packages were numbered, then weighed before and after filling to determine the amount of powder loaded. The filled blister packages were stored in a desiccating box operated at <2% RH until use. The powders were then tested for dispersibility from a DPI described in U.S. Pat. No. 5,740,794.

Emitted Dose testing of the formulations was assessed following USP guidelines for inhalation products. The actuated dose was collected using a 30 L min$^{-1}$ flow rate held for 2 seconds onto a type A/E glass filter (Gelman, Ann Arbor, Mich.). The emitted dose was calculated gravimetrically knowing the blister weight, total blister fill weight, and net change in filter weight.

Dry powder containing sodium chloride exhibited poor powder flow, and did not aerosolize well. In contrast, the formulation in which calcium chloride was substituted for the sodium chloride yielded particles with good flow and excellent emitted dose character. The differences in dispersibility between the two formulations is further reflected in the standard deviations of the emitted dose. The foregoing example illustrates the ability of the present invention to alter and modulate the flow and emission properties of dry lipid particles through the inclusion of calcium ions.

TABLE II

Formulation of Highly Dispersible Dry Powder Lung Surfactant Preparations

| Dry Powder Formulation | Ca/DSPC (mol/mol) | Emitted Dose (%) |
|---|---|---|
| "Exosurf" | 0 | 10 ± 33 |
| "Exosurf" + Calcium | 0.5 | 87 ± 3 |

EXAMPLE IV

Thermal Stability of Spray-Dried Phospholipid Particles

In the current example, the thermal stability of the spray-dried phospholipid particles prepared in example I were assessed. Accordingly 50 mg of powder was transferred into 20 mL glass vials and stored in a vacuum oven at 100° C. for 1 hour. The volume-weighted mass median diameters (MMD) for the powders were determined using a SympaTech laser diffraction analyzer (HELOS H1006, Clausthal-Zellerfeld, Germany) equipped with a RODOS type T4.1 vibrating trough. Approximately 1-3 mg of powder was placed in the powder feeder, which was subsequently atomized through a laser beam using 1 bar of air pressure, 60 mbar of vacuum, 70% feed rate and 1.30 mm funnel gap. Data was collected over an interval of 0.4 s, with a 175 μm focal length, triggered at 1% obscuration. Particle size distributions were determined using a Fraünhofer model. The volume-weighted mean aerodynamic diameters (VMAD) for the powders were determined with a model 8050 Aerosizer®LD particle size analysis system (Amherst Process Instruments, Hadley, Mass.) equipped with an Aero-Sampler® chamber. Approximately 0.2 mg of powder was loaded into a specially designed DPI testing apparatus. In this test, the powder was aerosolized by actuating a propellant can containing HFA-134a through the loaded sample chamber. The design of this apparatus is such to mimic actuation from an active DPI device and to offer some insight into powder flowability or its ability to deaggregate. Narrow particle size distributions are preferred and are believed to be an indication of the powder's ability to deaggregate.

Table III depicts the thermal stability and changes in particle size (MMD and VMAD) for the various spray-dried DSPC particles as a function of Ca/DSPC (mol/mol) ratio. The thermal stability of the powders was found to increase with increasing calcium content. Significant structural and particle size changes were observed for the formulation devoid of calcium ions, as evidenced by particle sintering and large increases in MMD and VMAD. The addition of small amounts of calcium ions (Ca/DSPC=0.25) resulting in a significant improvement in thermal stability of the phospholipid particles. More surprising, the spray-dried phospholipid formulation enriched at Ca/DSPC ratio of 0.5 completely tolerated the accelerated storage conditions, as no significant changes had occurred as a result of storage at 100° C. for 1 hour. The above example further illustrates the enhanced thermal stability of spray-dried phospholipid particles afforded by the inclusion of calcium ions.

TABLE III

Aerosol characteristics of Spray-Dried DSPC Powders following Storage at 100° C. for 1 hour

| Ca/DSPC (mol/mol) | Tm (° C.) | Thermal Stability | $MMD_0$ (μm) | $VMAD_0$ (μm) | MMD (μm) | VMAD (μm) |
|---|---|---|---|---|---|---|
| 0 | 79 | Sintering at 5 min. | 3.3 | 2.1 | 5.7 | 4.1 |
| 0.25 | 85 | Sintering at 45 min. | 3.4 | 1.8 | 4.5 | 2.1 |
| 0.5 | 98 | No Change | 3.6 | 1.7 | 3.5 | 1.8 |

EXAMPLE V

The Effect of Added Calcium Ions on pMDI Stability

The objective of this study was to examine the effect added calcium had on the physical stability of lipid-based pMDI suspensions to moisture. Budesonide powders were prepared by spray-drying a feed solution comprised of micronized drug particles suspended in the aqueous phase of a fluorocarbon-in-water emulsion. Accordingly, 0.8 g saturated egg phosphatidylcholine (EPC-3, Lipoid KG, Ludwigshafen, Germany) was dispersed in approximately 80 mL hot deionized water (T=80° C.) using an Ultra-Turrax mixer at 8000 rpm for 2 to 5 minutes. 20 g of perflubron ($\phi$=0.09) was then added drop wise during mixing. After the addition was complete, the emulsion was mixed for an additional period of not less than 4 minutes. The resulting coarse emulsion was homogenized under high pressure with an Avestin C-5 homogenizer (Ottawa, Canada) at 18,000 psi for 5 passes. The resulting submicron emulsion was then combined with a second aqueous phase containing 1.33 g budesonide suspended in a solution comprising 0.4 g d-lactose monohydrate, and 0-0.134 g calcium chloride dissolved in approximately 30 g of deionized water. The combined solution was then mixed using an Ultra-Turrax mixer at 8000 rpm for 2 minutes to ensure dispersion of the budesonide particles. Hollow porous budesonide particles were prepared by spray-drying the dispersion with a B-191 Mini Spray-Drier (Büchi, Flawil, Switzerland) under the following spray conditions: aspiration=80%, inlet temperature=85° C., outlet temperature=57° C., feed pump=2.3 mL/min, total air flow=22.4 SCFM. Free flowing white powders were collected at the cyclone separator. Scanning electron microscopic (SEM) analysis showed the powders to be spherical and highly porous.

Approximately 40 mg of spray-dried budesonide particles were weighed into 10 ml aluminum cans, and crimp sealed (Pamasol 2005/10, Pfaffikon, Switzerland) with a DF30/50 ACT 50 µl metering valve (Valois of America, Greenwich, Conn.). The canisters were charged with 5 g HFA-134a (DuPont, Wilmington, Del.) propellant by overpressure through the valve stem (Pamasol 8808). To elucidate differences between the budesonide formulations, propellant preparations that were spiked with varying amounts of water (0 to 1100 ppm) were utilized. The amount of the propellant in the can was determined by weighing the can before and after the fill. The final powder concentration in propellant was ~0.8% w/w and formulated to provide a theoretical ex-valve dose of 100 µg budesonide per actuation. Powder dispersion was achieved by placing the canisters in a sonication bath for 15 min. The charged pMDIs were placed in quarantine for a period of 7 days at ambient conditions to allow the valve seals to seat.

For the purpose of this study the aerosol fine particle fraction, FPF (%<5.8 µm) was used to assess changes in suspension physical stability that had occurred as a result of the water activity. The budesonide pMDIs were tested using commonly accepted pharmaceutical procedures. The method utilized was compliant with the United State Pharmacopeia (USP) procedure (Pharmacopeial Previews (1996) 22:3065-3098). After 5 waste shots, 20 doses from the test pMDIs were actuated into an Andersen Impactor. The extraction from all the plates, induction port, and actuator were performed in closed containers with an appropriate amount of methanol: water (1:1, v/v). The filter was installed but not assayed, because the polyacrylic binder interfered with the analysis. Budesonide was quantified by measuring the absorption at 245 nm (Beckman DU640 spectrophotometer) and compared to an external standard curve with the extraction solvent as the blank. The FPF was calculated according to the USP method referenced above.

The effect of added calcium ions on the physical stability of the budesonide pMDIs is depicted in FIG. I. The physical stability of the budesonide pMDIs was found to increase with increasing calcium concentration. Surprisingly the tolerance of the budesonide pMDI suspension to moisture increased from approximately 400 ppm to nearly 700 ppm by the inclusion of 4% calcium chloride into the formulation.

This example illustrates the enhanced stability of phospholipid-based pMDI particles afforded by the presence of calcium ions. The ability of a pMDI formulation to tolerate increased levels of moisture will lead to an enhancement in their long-term storage stability. The presence of water fuels structural changes, which can lead to formation of liquid bridges between particles and/or recrystallization of components and changes in surface characteristics. The overall effect of moisture ingress for suspension pMDIs leads to particle coarsening and suspension instability, all of which can lead to product failure.

EXAMPLE VI

The Effect of Added Calcium Ions on Particle Morphology

The objective of this study was to examine the effect added calcium has upon the morphological character of spray-dried phospholipid particles. Scanning electron micrographic (SEM) images of the spray-dried distearoylphosphatidylcholine particles prepared in example I were taken. The powders were placed on double sticky carbon graphite that was affixed on labeled aluminum stubs. The samples were then sputter-coated with a 250-300 Å layer of gold/palladium. Samples were examined on a scanning electron microscope operated at an accelerating voltage of 20 Kev, and a probe current of 250 pAmps. Photomicrographs were digitally captured at a 20,000× magnification.

The effect of calcium ion concentration on the morphology of spray-dried DSPC particles is illustrated in FIG. II. Formulations containing calcium ions had a highly porous sponge-like inflated morphology, whereas the neat DSPC particles appeared melted and collapsed. The hollow porous morphology is characterized by powders that flow and aerosolize well, whereas the collapsed morphology results in powders with poor flowability and dispersibility. No significant difference in morphology was observed as a result of calcium ion concentration, although the Ca/DSPC=0.25 formulation exhibited some degree of melted character as well. The decreased sensitivity of the powders with higher calcium content to melting and particle fusion is likely the result of the increased Tm values that allow for the powders to experience a higher drying temperature while maintaining the lipids in the gel state. The significant increases in Tm observed (Example I) lead to greater flexibility in spray-drying manufacture of these particles, and a significantly greater likelihood of achieving desired particle morphologies which are dependent on drying rates.

EXAMPLE VII

Preparation of Spray-Dried Budesonide Particles

Hollow porous budesonide particles were prepared by a two-step process. In the first step, 54 mg of budesonide (Vinchem, Chatham, N.J.), and 0.775 g of DSPC were dissolved in 2 ml of chloroform:methanol (2:1). The chloroform:methanol was then evaporated to obtain a thin film of the phospholipid/steroid mixture. The phospholipid/steroid mixture was then dispersed in 30.5 g of hot deionized water (T=60 to 70° C.) using an Ultra-Turrax mixer (model T-25) at 8000 rpm for 2 to 5 minutes. 12.8 g of perfluorooctyl ethane was then added dropwise during mixing. After the addition was complete, the emulsion was mixed for an additional period of not less than 4 minutes. The coarse emulsion was then passed through a high pressure homogenizer (Avestin, Ottawa, Canada) at 18,000 psi for 5 passes. The resulting submicron fluorocarbon-in-water with steroid solubilized in the lipid monolayer surrounding the droplets was utilized as the feedstock in for the second step, i.e. spray-drying on a B-191 Mini Spray-Drier (Büchi, Flawil, Switzerland). Calcium chloride (0 or 0.65 mg) was added in 2.5 g of water to the fluorocarbon-in-water emulsion immediately prior to spray drying. The following spray conditions were employed: aspiration=100%, inlet temperature=85° C., outlet temperature=60° C., feed pump=1.9 ml min$^{-1}$, atomizer pressure=60-65 psig, atomizer flow rate=30-35 cm. The aspiration flow (69-75%) was adjusted to maintain an exhaust bag pressure of 30-31 mbar. Free flowing white powders were collected using a standard cyclone separator.

The resulting dry budesonide particles were characterized using DSC. Each sample was analyzed in a modulated DSC mode under the following conditions: equilibration at −20° C., and 2° C./min ramp to 150° C. modulated +/−1° C. every 60 sec. The phospholipid Tm was defined as the peak maxima of the first endothermic transition from each reversing heat flow thermogram. The phospholipid Tm for DSPC particles without added calcium is 79° C. The addition of calcium ions in the budesonide formulation increased the Tm to 98° C. In addition, the powder formulations devoid of calcium had a cohesive flow character as compared to the calcium-enriched formulation.

The aerosol characteristics of the calcium containing formulation was examined in several passive dry powder inhaler devices (Eclipse®, Turbospin®, Cipla Rotahaler®, Glaxo Rotahaler®®, and Hovione FlowCaps®). The emitted dose was determined gravimetrically at comfortable inhalation flow rate (peak flow rate=20-62 L/min depending on the resistance of the device), and at a forced inhalation flow rate (peak flow rate 37-90 L/min). Under comfortable inhalation flow conditions the range of emitted doses was between 89 and 96% with a mean emitted dose of 94%. Under forced inhalation flow, the emitted dose varied between 94 and 103%, with a mean emitted dose of 99%. The fact that multiple devices with high and low resistance are able to effectively disperse the powders more or less independent of inspiratory flow rate speaks volumes to the dispersibility of the calcium containing budesonide powder tested.

The above example further illustrates the ability of the present powder engineering technology to effectively modulate the Tm through formulation changes. Increased (Tm's) are desired as they often indicate increased physical stability and improved powder dispersibility.

EXAMPLE VIII

Rapid Spreading of Spray-Dried DSPC Particles on an Air-Water Interface

The rapid spreading characteristics of the disclosed spray-dried phospholipid-based particles at the air/water interface are illustrated in FIG. III. Surface tension measurements were made on a Kruss K12 tensiometer at 25° C. using the Wilhemey plate technique. To measure surface tension, 20 mL of DI water or DSPC liposome dispersion was placed in the thermostatic beaker. The platinum plate was tared in the air and then dipped into the liquid and moved into the interface, after which measurements were taken. For spray-dried DSPC particle analysis, measurements for DI water were made and confirmed to be 72±1 mN/m. The glassware and plate were re-cleaned if the surface tension was not within expectation. Approximately 0.5 mg of dry DSPC crystal was sprinkled carefully onto the surface while the plate was dipped into the DI water. Measurements were started immediately after the powder was added. Care was taken to ensure dry powder did not adsorb to the plate. Measurements were ceased if any powder had contacted the plate surface. The equilibrium surface tension of distearoylphosphatidylcholine (DSPC) is ca. 22 mN/m. Aqueous based DSPC liposomes adsorbed very slowly at the air/water interface as evidenced by the fact that after 240 sec., the surface tension has not been significantly reduced. The slow adsorption for liposomes is due to the slow molecular diffusion of DSPC through the water phase, resulting from its extremely low solubility in water. Surprisingly, the adsorption of DSPC in the form of spray-dried DSPC particles is very fast, reducing the surface tension to equilibrium values within a few seconds. Moreover the inclusion of calcium ions had no effect on the spreading of surfactant properties of the DSPC particles. This rapid spreading and reduction of surface tension is indicative of what would likely occur upon contacting the spray-dried phospholipid particles with a wetted pulmonary membrane. Specifically, the present example provides a model for the effective delivery of synthetic lung surfactants and drugs to the lung.

EXAMPLE IX

Preparation of Nicotine Bitartrate Particles for pMDIs by Spray-Drying

Hollow porous nicotine bitartrate particles were prepared by a spray-drying technique with a B-191 Mini Spray-Drier (Büchi, Flawil, Switzerland) under the following spray conditions: aspiration: 80%, inlet temperature: 85° C.; outlet temperature: 56° C.; feed pump: 2.3 mL/min; air flow: 28 SCFM. The feed solution was prepared by mixing two solutions A and B immediately prior to spray drying.

Solution A: 5.2 g of hot water (T=50-60° C.) was used to dissolve 0.60 g of nicotine bitartrate (Sigma Chemicals, St. Louis Mo.), 0.127 g d-l lactose (Sigma Chemicals, St. Louis Mo.), and 90 mg calcium chloride dihydrate (Fisher Scientific, Fair Lawn, N.J.).

Solution B: A fluorocarbon-in-water emulsion stabilized by phospholipid was prepared in the following manner. The phospholipid, 0.69 g SPC-3 (Lipoid KG, Ludwigshafen, Germany) was dispersed in 29 g of hot deionized water (T=60 to 70° C.) using an Ultra-Turrax mixer (model T-25) at 8000 rpm for 2 minutes (T=60-70° C.). 30.2 g of perfluorooctyl ethane (F-Tech, Japan) was added dropwise during mixing. After the fluorocarbon was added, the emulsion was mixed for a period of not less than 5 minutes at 10000 rpm. The resulting coarse emulsion was then passed through a high pressure homogenizer (Avestin, Ottawa, Canada) at 18,000 psi for 5 passes.

Solutions A and B were combined and fed into the spray-dryer under the conditions described above. A free flowing white powder was collected at the cyclone separator. The geometric diameter of the nicotine bitartrate particles was confirmed by laser diffraction (Sympatech Helos H1006, Clausthal-Zellerfeld, Germany), where a volume weighted mean diameter (VMD) of 2.60 μm was found. Scanning electron microscopy (SEM) analysis showed the powders to be spherical and porous. Differential scanning calorimetry analysis of the dry particles (TA Instruments) revealed the Tm for the nicotine bitartrate in the powder to be 62° C., which is similar to what is observed for spray-dried neat material.

EXAMPLE X

Preparation of Phospholipid-Based Particles Containing Nicotine Bitartrate by Spray-Drying Hollow porous nicotine bitartrate particles were prepared by a spray-drying technique with a B-191 Mini Spray-Drier (Büchi, Flawil, Switzerland) under the following spray conditions: aspiration: 80%, inlet temperature: 85° C.; outlet temperature: 57° C.; feed pump: 2.3 mL/min; total air flow: 22.4 SCFM.

A fluorocarbon-in-water emulsion stabilized by phospholipid was first prepared. The phospholipid, 0.45 g SPC-3 (Lipoid KG, Ludwigshafen, Germany), was homogenized in 30 g of hot deionized water (T=60 to 70° C.) using an Ultra-Turrax mixer (model T-25) at 8000 rpm for 2 (T=60-70° C.). 15 g of perfluorooctyl ethane (F-Tech, Japan) was added dropwise at a rate of approximately 1-2 ml/min during mixing. After the fluorocarbon was added, the emulsion was mixed for a period of not less than 4 minutes. The resulting coarse emulsion was then processed through a high pressure homogenizer (Avestin, Ottawa, Canada) at 18,000 psi for 5 passes.

The emulsion was decanted into a beaker containing 8 mg sodium phosphate monobasic (Spectrum Chemicals, Gardena, Calif.) and 90 mg calcium chloride dihydrate (Fisher Scientific, Fair Lawn, N.J.). The emulsion was allowed to stir for approximately 5 min. The emulsion was then decanted into a beaker containing 0.225 g nicotine bitartrate (Sigma Chemicals, St. Louis Mo.) and was stirred for 5 minutes. The feed solution was fed into the spray-dryer under the conditions described above. A free flowing white powder was collected at the cyclone separator. The nicotine bitartrate particles had a volume-weighted mean aerodynamic diameter of 1.47 μm as determined by a time-of-flight analytical method (Aerosizer, Amherst Process Instruments, Amherst, Mass.). The geometric diameter of the nicotine bitartrate particles was determined by laser diffraction (Sympatech Helos H1006, Clausthal-Zellerfeld, Germany), where a volume weighted mean diameter (VMD) of 2.95 μm was found. Scanning electron microscopy (SEM) analysis showed the powders to be spherical and highly porous. Differential scanning calorimetry analysis of the dry particles (TA Instruments) revealed the Tm for the nicotine bitartrate in the powder was approximately 85° C.

This foregoing example illustrates the ability of the present powder engineering technology to effectively modulate the Tm through formulation changes

EXAMPLE XI

The preparation of lung surfactant powders with and without the use of blowing agents was investigated. The resultant powders were characterized as to aerosol properties.

Preparation of Powders

The annex solutions were prepared by mixing calcium or sodium chloride, cetyl alcohol, tyloxapol (Sigma), and Infasurf (ONY Inc.) as described in Table IV in a 20 ml glass vial to which was added an amount of hot deionized water (70° C.) (approximately 0.54 g of sodium chloride were used instead of calcium chloride in lots 1843-HS-03 and 04). The mixture was vortexed until all solids were fully dissolved. One lot, 1843-HS-04 used 200 ml ethanol as a solvent.

The emulsions were prepared by adding DPPC into a beaker to which was added an amount of 70° C. deionized water. The mixture was mixed in a mixer on low speed for approximately 2-3 minutes. When a blowing agent was used, PFOE was weighed out into a small flask and added dropwise into the DPPC/water mixture. The PFOE was added slowly over the course of 1-2 minutes and the mixture was then allowed to continue mixing for an additional 1-2 minutes. Emulsion details are listed in Table IV.

When a blowing agent was used, the DPPC/water/PFOE mixture was then immediately removed from the mixer and run through a homogenizer four times at 10,000-13,000 psi. The sample was then run through a homogenizer a fifth time at 13,000-17,000 psi.

The annex solution was then added to the DPPC/water or DPPC/water/PFOE emulsion with continued stirring on a hot plate set to the lowest temperature. The mixtures were kept at approximately 50° C. during spray drying, which was done at the conditions listed in Table V.

TABLE IV

Annex/Emulsion Formulation and Spray Drying Conditions

| | | | | Emulsion | | | Annex Solution | | | | | |
|---|---|---|---|---|---|---|---|---|---|---|---|---|
| Lot # | Atom. Press. (psi) | Out Temp, C. | Flow rate (ml/min) | DPPC (g) | PFOE (g) | Hot* DI Water (g) | Calcium Chloride (g) | Tyloxapol (g) | Cetyl Alcohol (g) | Hot* DI Water (g) | Infasurf (g) | Water (g), From Infasurf |
| 1843-HS-01 | 60 | 60 | 2.5 | 1.560 | 18.5 | 40.42 | 0.144 | 0.120 | 0.174 | 20 | | |
| 1843-HS-03 | 60 | 58 | 2.5 | 1.234 | 18.5 | 50 | | 0.092 | 0.138 | 10 | | |
| 1843-HS-04 | 70 | 43/44 | 5.0 | 1.236 | | 50 (cold) | | 0.093 | 0.138 | | | |
| 1843-HS-26 | 70 | 60 | 5.0 | 1.554 | | 180 | 0.145 | 0.120 | 0.176 | 20 | | |
| 1843-HS-35 | 56 | 59 | 2.5 | 0.937 | 14.0 | 35 | 0.043 | | | | 0.420 | 12 |
| 1843-HS-38 | 60 | 55 | 2.5 | 0.227 | 8.0 | 10 | 0.044 | | | | 0.630 | 18 |
| 1843-HS-50 | 56 | 57 | 2.5 | 1.555 | | 180 | 0.145 | 0.128 | 0.177 | 20 | | |
| 1843-HS-51 | | 50 | 1.5 | 1.165 | | 130 | 0.109 | 0.092 | 0.132 | 20 | | |
| 1843-HS-55 | 50 | 50 | 1.5 | 0.937 | | 140 | 0.043 | | | | 0.420 | 12 |
| 1843-HS-64 | 50 | 50 | 1.5 | 0.230 | | 88.2 | 0.044 | | | | 0.630 | 18 |
| 1843-HS-67 | 50 | 43 | 1.5 | 0.091 | | 78 | 0.091 | | | | 0.420 | 12 |

TABLE IV-continued Annex/Emulsion Formulation and Spray Drying Conditions

| | | | | Emulsion | | | Annex Solution | | | | | |
|---|---|---|---|---|---|---|---|---|---|---|---|---|
| Lot # | Atom. Press. (psi) | Out Temp, C. | Flow rate (ml/min) | DPPC (g) | PFOE (g) | Hot* DI Water (g) | Calcium Chloride (g) | Tyloxapol (g) | Cetyl Alcohol (g) | Hot* DI Water (g) | Infasurf (g) | Water (g), From Infasurf |
| 1843-HS-69 | 70 | 60 | 5.0 | 0.092 | | 48 | 0.091 | | | | 0.420 | 12 |
| 1843-HS-70 | 50 | 35 | 1.5 | 0.090 | | 48 | 0.090 | | | | 0.420 | 12 |
| 1843-HS-77 | 60 | 43 | 2.5 | 1.540 | 18.2 | 50 | 0.146 | | | 10 | | |
| 1843-HS-78 | 50 | 35 | 1.5 | 0.150 | | 48 | 0.030 | | | | 0.420 | 12 |
| 1876-HS-88 | 60 | 44 | 2.5 | 0.775 | 9.2 | 25 | 0.080 | 0.065 | 0.087 | 5 | | |
| 1876-HS-90 | 70 | 60 | 5.0 | 0.775 | 9.3 | 25 | 0.088 | 0.064 | 0.088 | 5 | | |
| 1876-HS-92 | 60 | 60 | 2.5 | 0.776 | 9.3 | 25 | 0.072 | 0.060 | 0.087 | 5 | | |
| 1959-HS-36 | 60 | 59 | 2.5 | 0.227 | 8.0 | 10 | 0.043 | | | | 0.630 | 18 |
| 1959-HS-39 | 70 | 57 | 5 | 0.200 | 8.0 | 10 | 0.075 | | | | 0.630 | 18 |
| 1959-HS-50 | 60 | 60 | 2.5 | 0.200 | 8.0 | 10 | 0.074 | | | | 0.630 | 18 |
| 1959-HS-51 | 70 | 57 | 5 | 0.212 | 9.0 | 60.35 | 0.074 | | | | 0.630 | 18 |

TABLE V

Aerosol Characteristics

| Lot # | Yield | Lipid: CaCl | Fill Weight | % Moisture | % ED | SD | % RSD | % Left | % Collected | MMAD | % <3.3 mm | aerosizer | MMD (SYMPA) |
|---|---|---|---|---|---|---|---|---|---|---|---|---|---|
| 1843-HS-01 | 43.0 | 2 | 2.2 | 4.453 | 86.7 | 2.15 | 2.5 | 2.00 | 90.81 | 3.43 | 46 | 1.287 | 2.83 |
| 1843-HS-03 | 36.0 | No CaCl | 2.2 | 2.205 | 10 | 3.28 | 32.7 | 17.98 | 16.80 | 5.5 | 14 | | |
| 1843-HS-04 | 19.0 | No CaCl | 5.0 | 1.235 | 7.3 | 2.18 | 30.0 | 30.54 | 10.89 | — | — | | |
| 1843-HS-26 | 35.4 | 2 | 5.0 | 5.563 | 66.26 | 7.15 | 10.8 | 4.05 | 69.16 | 3.65 | 44 | | |
| 1843-HS-26 | 35.4 | 2 | 2.2 | — | 82.44 | 4.11 | 5.0 | 11.07 | 92.70 | 2.90 | 57 | | — |
| 1843-HS-35 | 36.5 | 5.78 | 2.2 | 3.722, 2.89KF | 81.63 | 3.04 | 3.7 | 3.9 | 84.98 | 4.25 | 29 | 2.683/ 2.980 | 3.84/ 3.89 |
| 1843-HS-38 | 29.0 | 3.57 | 2.2 | 3.04 | 83.35 | 2.93 | 3.5 | 3.25 | 86.16 | 4.14 | 33 | 2.799 | 3.93 |
| 1843-HS-50 | 27.3 | 2 | not filled | — | — | — | — | — | — | — | — | — | — |
| 1843-HS-51 | 40.7 | 2 | 2.2 | 3.344 | 85.77 | 2.83 | 3.3 | 9.10 | 94.37 | 3.22 | 51 | | |
| 1843-HS-51 | 40.7 | 2 | 5.0 | — | 76.09 | 5.33 | 7.0 | 4.19 | 79.41 | 3.85 | 42 | | — |
| 1843-HS-55 | 58.0 | 5.78 | 2.2 | 2.058 | 67.87 | 10.67 | 15.7 | 5.66 | 71.85 | 3.45 | 46 | | |
| 1843-HS-64 | 11.5 | 1.79 | not filled | — | — | — | — | — | — | — | — | — | — |
| 1843-HS-67 | 27.8 | 1 | not filled | — | — | — | — | — | — | — | — | — | — |
| 1843-HS-69 | 11.6 | 1 | not filled | — | — | — | — | — | — | — | — | — | — |
| 1843-HS-70 | 40.4 | 1 | 2.2 | 3.254 | 54.55 | 5.05 | 9.3 | 8.29 | 59.54 | 3.51 | 45 | | |
| 1843-HS-78 | 52.0 | 3.40 | 2.2 | 2.237, 2.89KF | 69.87 | 11.72 | 16.8 | 2.78 | 71.77 | 3.74 | 39 | 3.07 | 3.98 |
| 1876-HS-88 | 51.0 | 3.57 | 2.2 | 5.050 | 83.71 | 8.69 | 10.4 | 7.47 | 90.45 | 3.57 | 45 | | 2.76/ 2.80/ 2.74 |
| 1876-HS-90 | 52.8 | 3.57 | 2.2 | 4.871 | 91.88 | 4.15 | 4.5 | 6.87 | 98.67 | 2.94 | 56 | | 2.16/ 2.16 |
| 1876-HS-92 | 47.3 | 3.57 | 2.2 | 5.066 | 93.31 | 2.58 | 2.8 | 5.13 | 98.40 | 3.28 | 50 | | 2.32/ 2.26 |
| 1959-HS-36 | 39.4 | 3.57 | 2.2 | 2.828 | 69.36 | 10.77 | 15.5 | 2.69 | 71.29 | 3.73 | 41 | — | 2.94/ 2.86 |
| 1959-HS-39 | 72.8 | 2 | 2.2 | | 83.52 | 3.06 | 3.7 | 3.33 | 86.46 | 3.63 | 43 | — | 2.68/ 2.67 |
| 1959-HS-50 | 23.3 | 2 | not filled | 3.150 | — | — | — | — | — | — | — | — | — |
| 1959-HS-51 | 72.7 | 2 | 2.2 | 4.954 | 85.19 | 1.66 | 2 | 2.11 | 83.5 | 3.71 | 43 | — | 2.36/ 2.44 |

EXAMPLE XII

Leuprolide Acetate Particles

A single feed solution is prepared under defined conditions. The feed solution is comprised of leuprolide acetate in the aqueous phase of a fluorocarbon-in-water emulsion. The emulsion composition is listed in Table VI below. Accordingly, DSPC and calcium chloride dihydrate are dispersed in approximately 400 mL SWFI (T=60-70 C) using an Ultra-Turrax T-50 mixer at 8000 rpm for 2 to 5 minutes. The perflubron is then added drop wise during mixing. After the addition is complete, the emulsion is mixed for an additional period of not less than 5 minutes at 10,000 rpm. The resulting coarse emulsion is then homogenized under high pressure with an Avestin C-5 homogenizer (Ottawa, Canada) at 19,000 psi for 5 discrete passes. The emulsion is transferred to the Potent Molecule Laboratory for Leuprolide Acetate addition and spray drying.

TABLE VI

Leuprolide Acetate Emulsion Composition

| Emulsion Components | Amount (grams) | % solids |
|---|---|---|
| DSPC | 7.33 | 73% |
| Calcium Chloride | 0.67 | 7% |
| Perflubron | 200 | NA |
| SWFI | 400 | NA |
| Leuprolide Acetate | 2.00 | 20% |

Aerosol Data:

Deposition analysis is performed using a multi-stage liquid impinger (MSLI). The apparatus consists of four concurrent stages and a terminal filter, each containing an aliquot of appropriate solvent for Leuprolide Acetate analysis. Deposition and emission data is reported in Table VII below.

TABLE VII

Leuprolide Acetate Aerosol Data

| Lot# | XB2316 |
|---|---|
| Device | Turbospin |
| Flow Rate | 60 Lpm |
| Emitted Dose | 96% |
| n = | 20 |
| MMAD | 2.40 |
| S4-Filter | 70% |
| n = | 4 |

EXAMPLE XIII

PTH Feed Solution Preparation

A single feed solution is prepared under defined conditions. The feed solution is comprised of parathyroid hormone in the aqueous phase of a fluorocarbon-in-water emulsion. The emulsion composition is listed in Table VIII below. Accordingly, DSPC and calcium chloride dihydrate are dispersed in approximately 40 mL SWFI (T=60-70 C) using an Ultra-Turrax T-50 mixer at 8000 rpm for 2 to 5 minutes. The perfluorooctylethane is then added drop wise during mixing. After the addition is complete, the emulsion is mixed for an additional period of not less than 5 minutes at 10,000 rpm. The resulting coarse emulsion is then homogenized under high pressure with an Avestin C-5 homogenizer (Ottawa, Canada) at 19,000 psi for 5 discrete passes. The active drug is added to the emulsion and subsequently spray dried after mixing for a period of not less than 10 minutes.

TABLE VIII

Parathyroid Hormone Emulsion Composition

| Emulsion Components | Amount (grams) | % solids |
|---|---|---|
| DSPC | 0.825 | 82.5% |
| Calcium Chloride | 0.075 | 7.5% |
| Perfluorooctylethane(PFOE) | 28 | NA |

TABLE VIII-continued

Parathyroid Hormone Emulsion Composition

| Emulsion Components | Amount (grams) | % solids |
|---|---|---|
| SWFI | 40 | NA |
| Parathyroid Hormone | 0.100 | 10% |

Aerosol Data:

Deposition analysis is performed using an Anderson Cascade Impactor. The apparatus consists of seven concurrent stages and a terminal filter. Aerosol deposition is measured gravimetrically and is reported in Table IX below.

TABLE IX

Parathyroid Hormone Aerosol Data

| Lot# | 2193-1 |
|---|---|
| Device | Turbospin |
| Flow Rate | 30 Lpm |
| MMAD | 2.67 |
| S4-Filter | 59% |
| n = | 2 |

EXAMPLE XIV

Preparation of Metered Dose Inhalers Containing Nicotine Bitartrate Particles 50 mg of nicotine bitartrate particles prepared in Examples IX, and X were weighed into 10 ml aluminum cans, crimp sealed a DF30/50 RCU-20cs 50 µl valve (Valois of America, Greenwich, Conn.) and charged with HFA-134a (DuPont, Wilmington, Del.) propellant by overpressure through the stem. A Pamasol (Pfaffikon, Switzerland) model 2005 small scale production plant complete with a model 2008 propellant pump was used for this purpose. The amount of the propellant in the can was determined by weighing the can before and after the fill. The final powder concentration in propellant was 0.5% w/w and formulated to provide an approximate emitted dose of 110 µg nicotine bitartrate.

EXAMPLE XV

Andersen Impactor Test for Assessing Nicotine Bitartrate pMDI Performance

The MDIs were tested using commonly accepted pharmaceutical procedures. The method utilized was compliant with the United State Pharmacopeia (USP) procedure (Pharmacopeial Previews (1996) 22:3065-3098) incorporated herein by reference. After 5 waste shots, 20 doses from the test pMDIs were actuated into an Andersen Impactor.

Extraction procedure. The extraction from all the plates, induction port, and actuator were performed in closed containers with an appropriate amount of methanol:water (1:1, v/v). The filter was installed but not assayed, because the polyacrylic binder interfered with the analysis. The mass balance and particle size distribution trends indicated that the deposition on the filter was negligibly small.

Quantitation procedure. Nicotine bitartrate was quantitated by measuring the absorption at 258 nm (Beckman DU640 spectrophotometer) and compared to an external standard curve with the extraction solvent as the blank.

Calculation procedure. For each MDI, the mass of the drug in the stem (component −3), actuator (−2), induction port (−1) and plates (0-7) were quantified as described above. The Fine Particle Dose and Fine Particle Fraction was calculated according to the USP method referenced above. Throat deposition was defined as the mass of drug found in the induction port and on plates 0 and 1. The mean mass aerodynamic diameters (MMAD) and geometric standard diameters (GSD) were evaluated by fitting the experimental cumulative function with log-normal distribution by using two-parameter fitting routine. The results of these experiments are presented in subsequent examples.

EXAMPLE XVI

Andersen Cascade Impactor Results for Nicotine Bitartrate pMDI Formulations

The results of the cascade impactor tests for the nicotine bitartrate pMDIs prepared according to Example XIV are shown below in Table X.

TABLE X

| | Nicotine Bitartrate pMDIs | | |
|---|---|---|---|
| | MMAD (GSD) μm | Fine particle fraction, % | Fine Particle Dose, μg |
| Nicotine/SPC-3/CaCl$_2$/Lactose | 3.6 (2.0) | 70 | 74 |
| Nicotine/SPC-3/CaCl$_2$/NaPhosphate | 3.0 (1.9) | 73 | 80 |

Both pMDI preparations were observed by visual inspection to have excellent suspension stability, where little or no creaming or sedimentation occurred over 1 hour. The lactose containing formulations had a slightly larger MMAD and lower FPF and FPD as compared with the sodium phosphate formulation. The reduction in aerosol performance for the lactose formulation could be due to increased water content as evidenced in the reduced Tm.

The invention has now been described in detail for purposes of clarity and understanding. However, it will be appreciated that certain changes and modifications may be practiced within the scope of the appended claims.

We claim:

1. A particulate composition for delivery to the pulmonary system, the composition comprising:
    particles comprising an active agent, a saturated phospholipid and a polyvalent cation, wherein the molar ratio of polyvalent cation to phospholipid is at least 0.05 and is sufficiently high to increase the gel-to-liquid crystal transition temperature of the particles compared to particles without the polyvalent cation such that the particles have a gel-to-liquid crystal transition temperature that is greater than room temperature by at least 20° C.

2. A particulate composition according to claim 1 wherein said gel-to-liquid crystal transition temperature is greater than room temperature by at least 40° C.

3. A particulate composition according to claim 1 further comprising a surfactant selected from the group consisting of nonionic detergents, nonionic block copolymers, ionic surfactants and combinations thereof.

4. A particulate composition according to claim 3 wherein the surfactant is selected from the group consisting of sorbitan esters, ethoxylated sorbitan esters, fatty acids, salts, sugar esters, ethylene oxides, and combinations thereof.

5. A particulate composition according to claim 1 wherein the polyvalent cation is a divalent cation.

6. A particulate composition according to claim 5 wherein the divalent cation is selected from the group consisting of calcium, magnesium and zinc.

7. A particulate composition according to claim 5 wherein the molar ratio of divalent cation to phospholipid is 0.05-2.0.

8. A particulate composition according to claim 5 wherein the molar ratio of divalent cation to phospholipid is 0.25-1.0.

9. A particulate composition according to claim 8 wherein the divalent cation is calcium.

10. A particulate composition according to claim 9 wherein the molar ratio of calcium to phospholipid is about 0.50.

11. A particulate composition according to claim 1 wherein the phospholipid comprises a natural or synthetic lung surfactant.

12. A particulate composition according to claim 1 wherein the active agent is selected from the group consisting of nicotine, human growth hormone, parathyroid hormone, leuprolide, budesonide, tobramycin, albuterol, insulin, interferon alpha, interferon beta, amphotericin, fluticasone, salmeterol, formoterol, and salts thereof.

13. A particulate composition according to claim 1 further comprising a polymer selected from the group consisting of polysaccharides, polyvinyl alcohol, polyvinyl pyrrolidone, polylactides, polyglycolides, polyethylene glycol, and mixtures thereof.

14. A particulate composition according to claim 1 comprising particles having a mass median diameter of less than 20 microns.

15. A particulate composition according to claim 14 wherein the mass median diameter is within 0.5-5 microns.

16. A particulate composition according to claim 14 wherein the particles comprise an aerodynamic diameter of less than 10 microns.

17. A particulate composition according to claim 16 wherein the aerodynamic diameter is within 0.5-5 microns.

18. A particulate composition according to claim 1 comprising an emitted dose of at least 40%.

19. A particulate composition according to claim 1 comprising an emitted dose of at least 60%.

20. A particulate composition according to claim 1 comprising an emitted dose of at least 90%.

21. A particulate composition according to claim 1 further comprising a non-aqueous suspension medium.

22. A particulate composition according to claim 1 further comprising an excipient selected from the group consisting of amino acids, carbohydrates, inorganic salts, organic salts, carboxylic acids, and mixtures thereof.

23. A particulate composition according to claim 22 wherein the excipient is selected from the group consisting of hydrophobic amino acids, monosaccharides, disaccharides, polysaccharides, sodium citrate, citric acid, ammonium carbonate, ammonium acetate, and ammonium chloride.

24. A particulate composition according to claim 1 wherein the bulk density of the particulate composition is less than 0.5 g/cm$^3$.

25. A particulate composition according to claim 24 wherein the bulk density of the particulate composition is less than 0.05 g/cm$^3$.

26. A particulate composition comprising:
    particles comprising an active agent, a saturated phospholipid and a polyvalent cation, wherein the molar ratio of polyvalent cation to phospholipid is at least 0.05 and wherein the particles have a gel-to-liquid transition temperature at least 20° C. higher than room temperature.

27. A particulate composition for delivery to the pulmonary system, the composition comprising porous particles comprising:
20-99.9% of a saturated phospholipid;
a polyvalent cation; and
0.1-80% active agent;
wherein the molar ratio of polyvalent cation to phospholipid is at least 0.05 and is sufficiently high to increase the gel-to-liquid crystal transition temperature of the particles compared to particles without the polyvalent cation such that the particles have a gel-to-liquid crystal transition temperature that is greater than room temperature by at least 20° C.

28. A method of delivering an active agent to a patient in need thereof, the method comprising:
administering to the respiratory tract of the patient an effective amount of particles comprising an active agent, a saturated phospholipid and a polyvalent cation, wherein the molar ratio of polyvalent cation to phospholipid is at least 0.05 and is sufficiently high to increase the gel-to-liquid crystal transition temperature of the particles compared to particles without the polyvalent cation such that the particles have a gel-to-liquid crystal transition temperature that is greater than room temperature by at least 20° C.

29. A method according to claim 28 wherein the particulate composition comprises particles having a mass median diameter of less than 20 microns.

30. A method according to claim 29 wherein the mass median diameter is within 0.5-5 microns.

31. A method according to claim 29 wherein the particles comprise an aerodynamic diameter of less than 10 microns.

32. A method according to claim 31 wherein the aerodynamic diameter is within 0.5-5 microns.

33. A method according to claim 28 wherein the particles comprise polyvalent cation at a molar ratio of polyvalent cation:phospholipid of 0.25-1.0.

34. A method according to claim 33 wherein the polyvalent cation comprises calcium.

35. A method according to claim 32 wherein the particles comprise a bulk density of less than 0.5 g/cm$^3$.

36. A method according to claim 35 wherein the active agent is selected from the group consisting of nicotine, human growth hormone, parathyroid hormone, leuprolide, budesonide, tobramycin, albuterol, insulin, interferon alpha, interferon beta, amphotericin, fluticasone, salmeterol, formoterol, and salts thereof.

37. A particulate composition according to claim 1 wherein the particles are hollow and porous.

38. A particulate composition according to claim 1 comprising 0.1-80% w/w of the active agent.

39. A particulate composition according to claim 26 wherein the particles are hollow and porous.

40. A particulate composition according to claim 26 wherein the particles have a gel-to-liquid transition temperature of at least 40° C. higher than room temperature.

41. A particulate composition according to claim 26 wherein the phospholipid is selected from dipalmitoylphosphatidylcholine or distearoylphosphatidylcholine.

42. A particulate composition comprising:
particles comprising a structural matrix comprising a saturated phospholipid and a polyvalent cation, wherein the molar ratio of polyvalent cation to phospholipid is at least 0.05 and is sufficiently high to increase the gel-to-liquid crystal transition temperature of the particles compared to particles without the polyvalent cation such that the particles have a gel-to-liquid crystal transition temperature that is greater than room temperature by at least 20° C., and wherein the particles further comprise an active agent.

43. A particulate composition according to claim 42 wherein the phospholipid comprises dipalmitoylphosphatidylcholine or distearoylphosphatidylcholine.

44. A particulate composition according to claim 42 wherein the polyvalent cation is a divalent cation.

45. A particulate composition according to claim 44 wherein the divalent cation is selected from the group consisting of calcium, magnesium, and zinc.

46. A particulate composition according to claim 42 wherein the molar ratio of polyvalent cation to phospholipid is 0.05-2.0.

47. A particulate composition according to claim 42 wherein the molar ratio of polyvalent cation to phospholipid is 0.25-1.0.

48. A particulate composition according to claim 42 wherein the active agent is selected from the group consisting of nicotine, human growth hormone, parathyroid hormone, leuprolide, budesonide, tobramycin, albuterol, insulin, interferon alpha, interferon beta, amphotericin, fluticasone, salmeterol, formoterol, and salts thereof.

49. A particulate composition according to claim 44 wherein the divalent cation is calcium.

50. A particulate composition according to claim 49 wherein the molar ratio of calcium to phospholipid is about 0.50.

51. A particulate composition according to claim 42 wherein the particles have a gel-to-liquid crystal transition temperature at least 20° C. higher than room temperature.

52. A particulate composition according to claim 42 wherein the particles have a gel-to-liquid crystal transition temperature at least 40° C. higher than room temperature.

53. A particulate composition according to claim 1 wherein the phospholipid is a zwitterionic phospholipid.

54. A particulate composition according to claim 26 wherein the phospholipid is a zwitterionic phospholipid.

55. A particulate composition according to claim 27 wherein the phospholipid is a zwitterionic phospholipid.

56. A particulate composition according to claim 27 wherein the molar ratio of polyvalent cation to phospholipid is effective to increase the gel to liquid crystal transition temperature of the particles compared to particles without the polyvalent cation.

57. A particulate composition according to claim 27 wherein the particles are hollow.

58. A method according to claim 28 wherein the phospholipid is a zwitterionic phospholipid.

59. A particulate composition according to claim 42 wherein the phospholipid is a zwitterionic phospholipid.

60. A particulate composition for delivery to the pulmonary system, the composition comprising:
particles comprising an active agent, a saturated phospholipid and a polyvalent cation, wherein the molar ratio of polyvalent cation to phospholipid is at least 0.05 and less than 2, whereby the gel-to-liquid crystal transition temperature of the particles is higher than particles without the polyvalent cation, and is greater than room temperature by at least 20° C.

61. A particulate composition according to claim 60 wherein the molar ratio of divalent cation to phospholipid is from 0.25 to 1.

62. A particulate composition according to claim 60 wherein the polyvalent cation is a divalent cation.

63. A particulate composition according to claim 62 wherein the divalent cation is selected from the group consisting of calcium, magnesium and zinc.

64. A particulate composition according to claim 62 wherein the divalent cation is calcium.

65. A particulate composition according to claim 64 wherein the molar ratio of calcium to phospholipid is about 0.50.

66. A particulate composition according to claim 60 wherein the gel-to-liquid crystal transition temperature is greater than a storage temperature for the particulate composition by at least 20° C.

67. A particulate composition according to claim 60 further comprising a surfactant selected from the group consisting of nonionic detergents, nonionic block copolymers, ionic surfactants and combinations thereof.

68. A particulate composition according to claim 60 wherein the particles have a mass median diameter of less than 20 microns and an aerodynamic diameter of less than 10 microns.

69. A particulate composition according to claim 60 further comprising an excipient selected from the group consisting of amino acids, carbohydrates, inorganic salts, organic salts, carboxylic acids, and mixtures thereof.

70. A particulate composition according to claim 60 wherein the bulk density of the particulate composition is less than 0.5 $g/cm^3$.

71. A method of making a temperature stable particulate composition for delivery to the pulmonary system, the method comprising:

(a) forming a feedstock comprising a saturated phospholipid emulsion and an active agent;

(b) adding a polyvalent cation to the feedstock in an amount sufficient to provide a molar ratio of polyvalent cation to phospholipid in the feedstock that is at least 0.05 and less than 2; and (c) drying the polyvalent cation containing feedstock to form porous particles having a gel-to-liquid crystal transition temperature that is higher than a storage room temperature of the porous particles by at least about 20° C.

72. A method according to claim 71 wherein (b) comprises adding the polyvalent cation to the feedstock in an amount sufficient to provide a molar ratio of polyvalent cation to phospholipid in the feedstock that is from 0.25 to 1.

73. A method according to claim 71 wherein the polyvalent cation is a divalent cation.

74. A method according to claim 73 wherein the divalent cation is selected from the group consisting of calcium, magnesium and zinc.

75. A method according to claim 73 wherein the divalent cation is calcium.

76. A method according to claim 71 further comprising adding to the feedstock, a surfactant selected comprising nonionic detergents, nonionic block copolymers, ionic surfactants and combinations thereof.

77. A method according to claim 71 further comprising adding to the feedetock a polymer selected from the group consisting of polysaccharides, polyvinyl alcohol, polyvinyl pyrrolidone, polylactides, polyglycolides, polyethylene glycol, and mixtures thereof.

78. A method according to claim 71 comprising drying the polyvalent ion comprising feedstock wherein the particles have a mass median diameter of less than 20 microns and an aerodynamic diameter of less than 10 microns.

79. A method according to claim 71 comprising adding an excipient to the feedstock, the excipient comprising amino acids, carbohydrates, inorganic salts, organic salts, carboxylic acids, and mixtures thereof.

80. A method according to claim 71 comprising drying the polyvalent cation comprising feedstock to provide a bulk density of the porous particles that is less than 0.5 $g/cm^3$.

* * * * *